US008346349B2

(12) United States Patent
Guttag et al.

(10) Patent No.: US 8,346,349 B2
(45) Date of Patent: Jan. 1, 2013

(54) METHOD AND APPARATUS FOR PREDICTING PATIENT OUTCOMES FROM A PHYSIOLOGICAL SEGMENTABLE PATIENT SIGNAL

(75) Inventors: John V. Guttag, Lexington, MA (US); Zeeshan H. Syed, Wayzata, MN (US); Philip Pohong Sung, Saratoga, CA (US); Collin M. Stultz, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 914 days.

(21) Appl. No.: 12/321,239

(22) Filed: Jan. 15, 2009

(65) Prior Publication Data
US 2009/0192394 A1   Jul. 30, 2009

Related U.S. Application Data

(60) Provisional application No. 61/021,510, filed on Jan. 16, 2008.

(51) Int. Cl.
*A61B 5/04* (2006.01)
(52) U.S. Cl. .................................................. 600/509
(58) Field of Classification Search ........... 600/509–525
See application file for complete search history.

(56) References Cited

U.S. PATENT DOCUMENTS

| 7,031,765 | B2* | 4/2006 | Ritscher et al. ............... 600/518 |
| 7,069,070 | B2* | 6/2006 | Carlson et al. ............... 600/519 |
| 7,539,532 | B2* | 5/2009 | Tran ............................. 600/509 |
| 7,599,733 | B1 | 10/2009 | Wirasinghe et al. |
| 7,949,389 | B2 | 5/2011 | Wolfberg et al. |
| 8,046,058 | B2* | 10/2011 | Lin et al. ..................... 600/509 |
| 2001/0034488 | A1 | 10/2001 | Policker et al. |

(Continued)

FOREIGN PATENT DOCUMENTS

WO    94/06350    3/1994

(Continued)

OTHER PUBLICATIONS

Tuzcu et al., "Dynamic Time Warping As a Novel Tool in Pattern Recognition of ECG Changes in Heart Rhythm Disturbances," *Systems, Man and Cybernetics*, 2005 IEEE International Conference on, IEEE, Piscataway, NJ, USA, vol. 1, Oct. 10, 2005, pp. 182-186.

(Continued)

*Primary Examiner* — Carl H Layno
*Assistant Examiner* — Paula J Stice
(74) *Attorney, Agent, or Firm* — K&L Gates LLP

(57) ABSTRACT

A method and apparatus for predicting patient outcome from a physiological segmentable signal of a patient. In one embodiment, the method comprises the steps of obtaining the physiological segmentable signal of the patient; segmenting the physiological segmentable signal into a plurality of separate segmentable components; calculating a time series of the morphological distance between adjacent separate segmentable components of the plurality of separate segmentable components; and predicting patient outcome in response to the time series of the morphological distance. In another aspect, the invention relates to a method for extracting information from physiological signals for one or more subjects including the steps of partitioning the physiological signal into a plurality of components, grouping the components into a plurality of information classes, assigning a unique symbol to each information class, mapping each component to the assigned symbol, and examining one or more such sequences for clinical significance.

58 Claims, 11 Drawing Sheets
(3 of 11 Drawing Sheet(s) Filed in Color)

U.S. PATENT DOCUMENTS

| | | |
|---|---|---|
| 2002/0103512 A1 | 8/2002 | Echauz et al. |
| 2003/0204146 A1 | 10/2003 | Carlson |
| 2004/0068199 A1 | 4/2004 | Echauz et al. |
| 2004/0147815 A1 | 7/2004 | Skinner |
| 2004/0176696 A1 | 9/2004 | Mortara |
| 2005/0010124 A1 | 1/2005 | Couderc et al. |
| 2005/0085734 A1* | 4/2005 | Tehrani .................. 600/484 |
| 2006/0056655 A1* | 3/2006 | Wen et al. .............. 382/103 |
| 2008/0097537 A1 | 4/2008 | Duann et al. |
| 2010/0016748 A1 | 1/2010 | Syed et al. |

FOREIGN PATENT DOCUMENTS

| | | |
|---|---|---|
| WO | 00/10455 | 3/2000 |

OTHER PUBLICATIONS

Vullings et al., "Automated ECG segmentation with Dynamic Time Warping," *Engineering in Medicine and biology Society*, 1998, Proceedings of the 20th Annual International Conference of the IEEE Hong Kong, China Oct. 29-Nov. 1, 1998, Piscataway, NJ, USA, IEE, US, pp. 163-166.

Vyklicky et al., "Analysis of dynamic changes in ECG Signals during Optical Mapping by Dynamic Time Warping," *Computers in Cardiology*, 2005, Lyon, France, Sep. 25-28, 2005, Piscataway, NJ, USA, IEEE, Sep. 25, 2005, pp. 543-546.

International Search Report and Written Opinion of the International Searching Authority for International Application No. PCT/US2009/000279, mailed Apr. 15, 2009 (19 pgs.).

Syed et al., "ECG Markers to Predict Cardiovascular Death: Heart Rate Variability, Deceleration Capacity and Morphologic Variability in Non-ST-Elevation ACS from the Merlin TIMI-36 Trial," American Heart Association Scientific Sessions, New Orleans, LA, Nov. 14-18, 2008.

Syed et al., "Morphologic Variability: A new Elecrocardiographic Technique for Risk Stratification After NSTEACS," American Heart Association Scientific Sessions, Orlando, FL, Nov. 4-7, 2007.

* cited by examiner (a) (b)

Traditional Recurrence Relation

$$\gamma(i,j) = d(i,j) + \min \begin{cases} \gamma(i-1, j-1) \\ \gamma(i-1, j) \\ \gamma(i, j-1) \end{cases}$$

(a)

Modified Recurrence Relation

$$\gamma(i,j) = d(i,j) + \min \begin{cases} \gamma(i-1, j-1) \\ d(i-1, j) + \gamma(i-2, j-1) \\ d(i-1, j) + d(i-2, j) + \gamma(i-3, j-1) \\ d(i, j-1) + \gamma(i-1, j-2) \\ d(i, j-1) + d(i, j-2) + \gamma(i-1, j-3) \end{cases}$$

(b)

METHOD AND APPARATUS FOR PREDICTING PATIENT OUTCOMES FROM A PHYSIOLOGICAL SEGMENTABLE PATIENT SIGNAL

RELATED APPLICATIONS

This application claims priority to provisional application Ser. No. 61/021,510 filed Jan. 16, 2008, which is herein incorporated in its entirety by reference.

FIELD OF THE INVENTION

The invention relates in general to a computer aided method of predicting patient outcomes and more specifically to an apparatus and method for predicting patient outcomes in response to physiological signals from the patient.

BACKGROUND OF THE INVENTION

The prediction of a patient outcome has been the goal of physicians for many years. For example, the evaluation of the surface electrocardiogram (ECG), in particular the QRS morphology and ST segment of the heartbeat, is central to the diagnosis, management and prognosis of patients with acute coronary syndromes or ACS. In most cases, clinical care focuses on an examination by a physician of an ECG and any arrhythmias detected on continuous monitoring. Several techniques have been described to measure specific aspects of the electrocardiographic signal and perform relatively complex analyses, including: heart rate variability (HRV), heart rate turbulence (HRT), T-wave alternans (TWA), signal averaged ECG (SAECG), and QT dispersion.

A number of these methods have been shown to provide benefit with respect to identifying high risk patients post ACS. For example, in ACS several studies suggest that HRV alone (both frequency and time domain measures) can be used to predict cardio-vascular mortality in patients who have had a recent myocardial infarction (MI). HRT has also been shown to identify patients at high-risk of death post MI. Both SAECG and TWA can identify patients at increased risk for ventricular arrhythmias post myocardial infarction. In sum, these techniques provide incremental benefit in identifying patients at high risk of subsequent cardiovascular events and may offer insight into pathological changes in the different components of cardiac activation and repolarization.

Many of these techniques focus on specific aspects of the electrocardiogram. T-wave alternans, for example, analyzes beat-to-beat changes in the T-wave amplitude, while ignoring other aspects of the ECG signal, in an attempt to classify patients who are at high risk for future adverse events. Similarly, HRV focuses on beat-to-beat variations in R-R intervals to calculate quantitative estimates of cardiovascular risk. Hence two ECG signals will yield the same calculated HRV measure if they have the same distribution of R-R intervals, regardless of whether the QRS complexes and ST-T wave segments have different morphologies.

This invention relates to an assessment of the entire physiological segmentable signal (for example the entire ECG beat (P wave-to-T wave)) to provide added information that can be used to identify high-risk patient subgroups.

SUMMARY OF THE INVENTION

The invention relates in one aspect to a method of predicting patient outcome from a segmentable physiological signal of a patient. The method includes the steps of: obtaining the physiological signal of the patient; removing noise and baseline wander from the signal, segmenting the physiological signal into a plurality of separate components; rejecting some number of components; calculating a time series of the morphological distance between adjacent separate components of the plurality of separate components; and predicting patient outcome in response to the time series of the morphological distance In one embodiment the segmentable physiological signal is an ECG and each component is a heartbeat. In another embodiment, a higher variability of morphologic distance indicates a higher probability of a worse patient outcome. In yet another embodiment the morphologic distance between adjacent heartbeats is determined by the energy difference in the adjacent heartbeats. In still yet another embodiment the morphological difference between adjacent beats is determined by physiological dynamic time warping. In another embodiment the predicted patient outcome is selected from a group consisting of death, arrhythmia, myocardial ischemia, and myocardial infarction In one embodiment the method further comprises the step of predicting patient outcome in response to combining morphologic distance variability with one or more other clinical predictors. In another embodiment the other clinical predictor is a TIMI or GRACE risk assessment. In another embodiment the other clinical predictor is derived from medical imaging. In another embodiment the other clinical predictor is derived from biomarkers. In another embodiment the other clinical predictor is derived from baseline clinical characteristics. In still yet another embodiment the step of predicting patient outcome is performed with an ECG risk measure calculated in response to morphological distance variability and other ECG-based measures. In another embodiment the step of predicting patient outcome is performed with an overall risk measure calculated in response to the ECG risk measure and a plurality of other metrics.

In another aspect the invention relates to a method of predicting patient outcome from a segmentable physiological signal of a patient by obtaining the signal of the patient; segmenting the physiological segmentable signal into a plurality of separate components; calculating a time series of the morphological distance between adjacent separate components of the plurality of separate components; summarizing the information in the time series; predicting patient outcome in response to the summarized time series information.

In one embodiment the step of summarizing of time series information comprises calculating a ratio of low frequency power to high frequency power for the time series. In another embodiment the summarizing of the time series information comprises calculating energy in a diagnostic frequency range.

In another aspect the invention relates to a system for predicting patient outcome from a segmentable physiological signal of a patient. In one embodiment the system includes a processor performing the operations of: obtaining the physiological signal of the patient; segmenting the physiological signal into a plurality of separate components; calculating a time series of the morphological distance between adjacent separate components of the plurality of separate components; and predicting patient outcome in response to the time series of the morphological distance In another embodiment the segmentable physiological signal is an ECG and where each component is a heartbeat. In yet another embodiment the higher the variability of morphologic distance predicts long and/or short term patient outcomes. In yet another embodiment an energy difference between adjacent beats is determined by physiological dynamic time warping.

In another aspect the invention relates to a system for predicting patient outcome from a segmentable signal of a patient. In one embodiment the system includes a processor performing the operations of: obtaining the physiological signal of the patient; segmenting the physiological signal into a plurality of separate components; calculating a time series of the morphological distance between adjacent separate components of the plurality of separate components; summarizing the information in the time series; predicting patient outcome in response to the summarized time series information.

A method for extracting information from physiological signals including the steps of partitioning the physiological signal into a plurality of components, grouping the components into a plurality of information classes, assigning a unique symbol to each information class, mapping each component to the assigned symbol, and examining the resulting symbolic sequence for clinical significance. In one embodiment, the physiological signal is an ECG signal and each component is a heartbeat. In another embodiment, the physiological signal is a respiration signal and each component is a breath. In another embodiment, the physiological signal is a blood pressure waveform and each component is a pulse. In another embodiment, the physiological signal is an EEG signal and each component represents a unit of time.

In yet another embodiment, one of the information classes is derived from information in the time and frequency domains. In still yet another embodiment, the information class is derived from at least one of: standard features of clinical significance and non-standard features of clinical significance. In another embodiment, the symbolic sequence has significance due to at least one of: the number of distinct symbols represented and the distribution of symbols represented and the symbolic sequence has significance due to one of its entropy and the pattern of symbols represented. In another embodiment, the components are grouped into information classes using clustering. In still yet another embodiment, the plurality of components is grouped into one of a predetermined number of information classes and a number of information classes which is not predetermined. In another embodiment, the method further includes the step of associating a representative component to each information class. In yet another embodiment, the information class is formed using a clustering technique and the representative component is the centroid of the cluster.

Another aspect of the invention relates to a system for extracting information from physiological signals comprising a processor. The processor partitions the physiological signal into a plurality of components; groups the components into a plurality of information classes; assigns a unique symbol to each information class; maps each component to the assigned symbol; and examines the resulting symbolic sequence for clinical significance. In one embodiment, the physiological signal is an ECG signal and each component is a heartbeat. In another embodiment, the physiological signal is a respiration signal and each component is a breath.

In yet another embodiment, the information class is derived from information in one of the time and frequency domains. In another embodiment, the information class is one of standard clinical significance and non-standard clinical significance. In another embodiment, the symbolic sequence has significance due to at least one of: the number of distinct symbols represented and the distribution of symbols represented. In another embodiment, the symbolic sequence has significance due to one of its entropy and the pattern of symbols represented.

In still yet another embodiment, the components are grouped into information classes using clustering. In another embodiment, the plurality of components is grouped into a predetermined number of information classes or into a number of information classes which is not predetermined. In another embodiment, the processor also associates a representative component to each information class. In still yet another embodiment, the representative component is the centroid of a cluster.

In yet another embodiment, the method includes repeating the steps for a plurality of patients having a common event of interest and examining the symbolic series for commonalities of common event of interest. In another embodiment, the commonality is a pattern that is approximately conserved preceding the event. In another embodiment, the examination of the symbolic series is performed on signals from different time periods for the same patient or signals from different patients. In another embodiment, the examination is performed using locality sensitive hashing, clustering using a 2-approximate solution to the k-center problem or sequential statistics.

In one embodiment, the method further includes associating a representative component to each information class and performing matching by looking at differences among the representative components, the distribution of symbols, or hidden Markov models.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is pointed out with particularity in the appended claims. The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE EMBODIMENTS OF THE INVENTION

Figure 1:
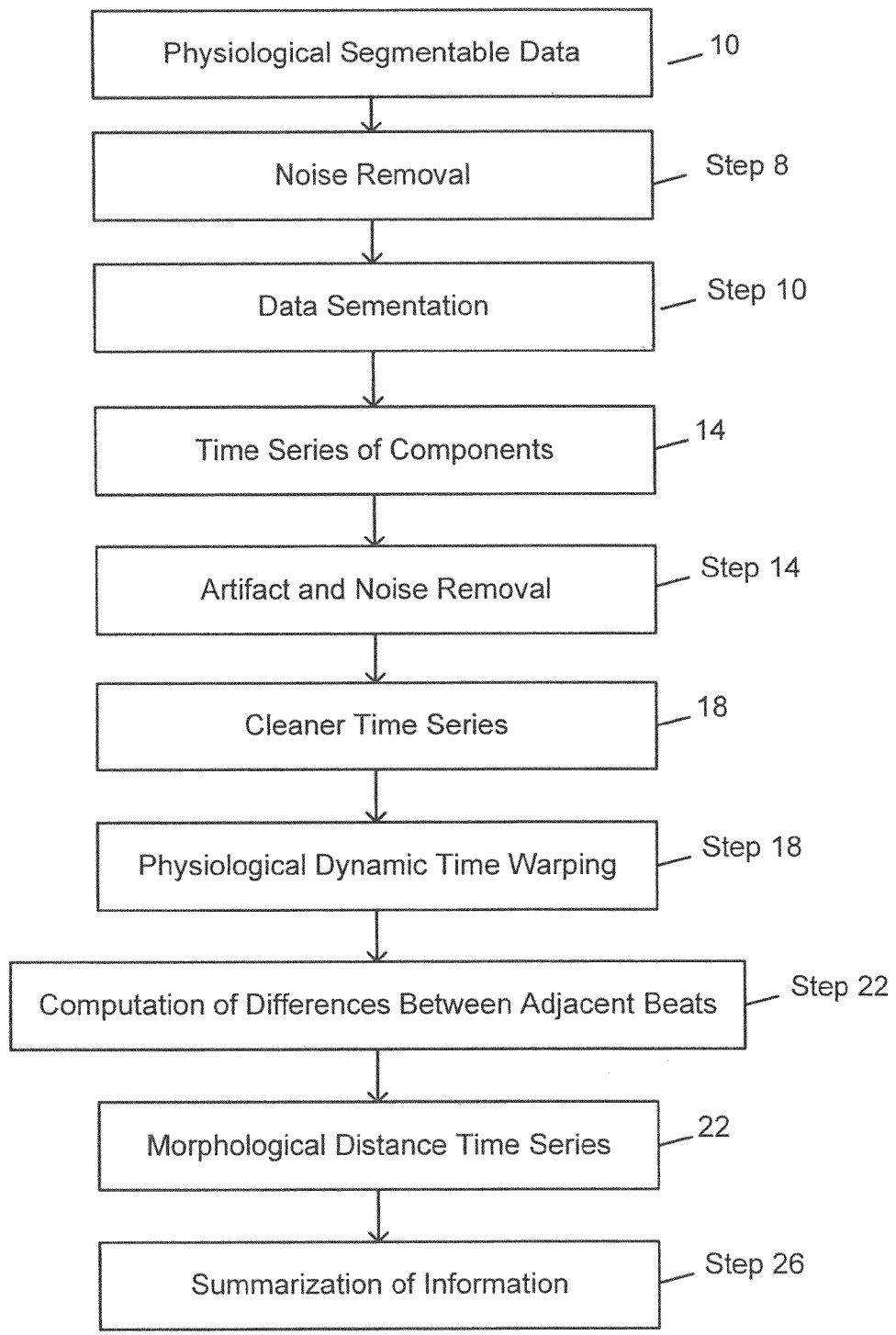
FIG. 1 is a flow chart of the overview of the steps of an embodiment of the invention.

In brief overview and referring to FIG. 1, an embodiment of the method of the invention begins with a segmentable physiological signal 10, such as an electrocardiogram or ECG. Other potential signals include but are not limited to respiration, blood pressure and electroencephalogram signals. These signals may be pre-recorded or obtained in real time. After cleaning (Step 8), the physiological signal is then segmented (Step 10) into a time series of components 14. For example, in the case of an ECG, a component is a heartbeat.

Components with certain properties are then removed (Step 14) from the time series to produce a cleaned time series (Step 18). Next physiological dynamic time warping, which is described below, is applied to the clean time series (Step 18) to generate a physiological dynamic time warped series. A computation is then made to measure the differences between adjacent components, such as beats (Step 22) to thereby generate a morphological distance time series 22, and summarize the differences between adjacent components (Step 26).

Figure 2:
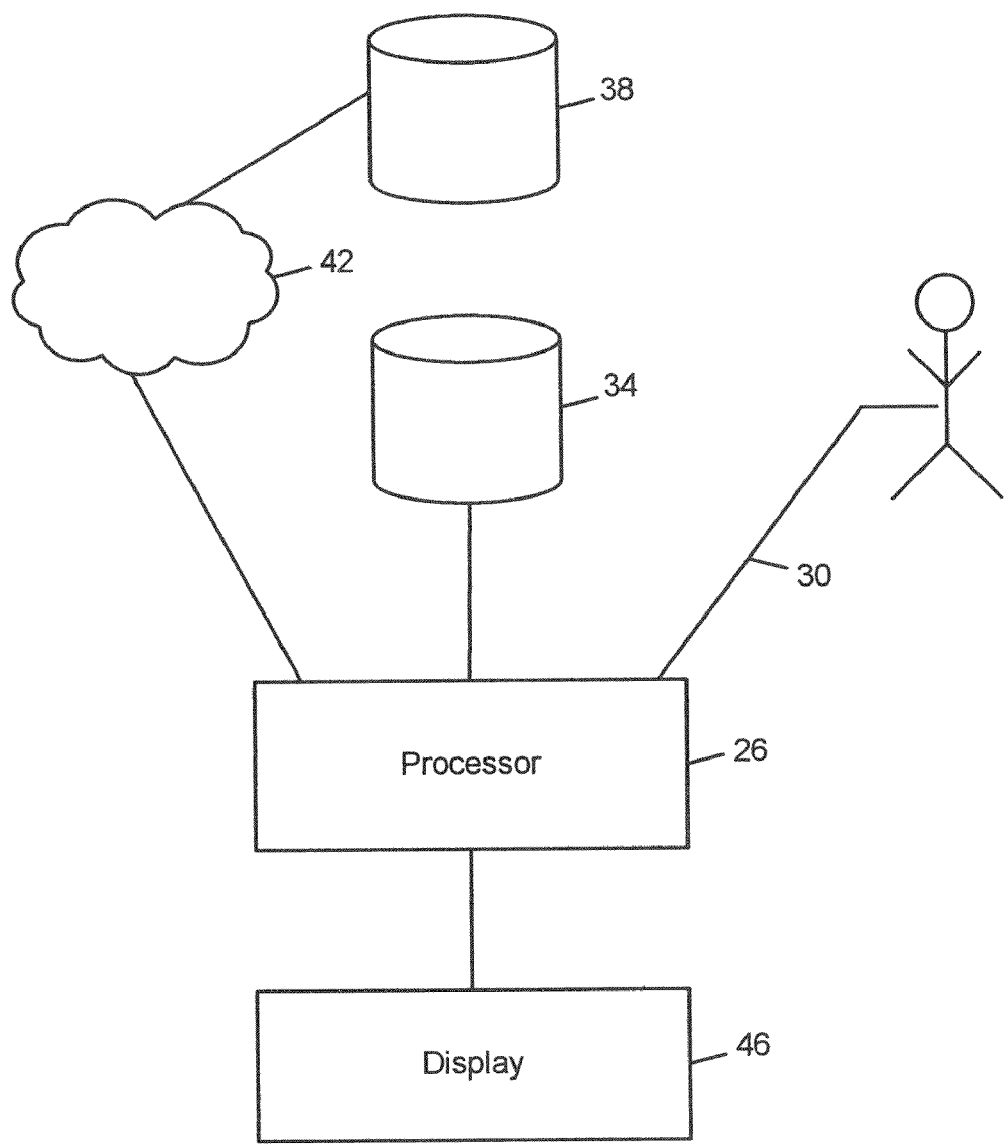
FIG. 2 is a diagram of an embodiment of a system of the invention used to perform the steps of FIG. 1.

Referring to FIG. 2, an embodiment of a system for performing the method of FIG. 1, includes a display 46, a processor 26 receiving signal data either in real time from an ECG device 30, as stored prerecorded data on a storage device 34, or across a network connection 42 to a remote source 38.

In more detail and using an ECG as a non-limiting example of a type of physiological signal, in one embodiment, a three lead continuous ECG monitoring system with a sampling rate of 128 Hz is used to take an ECG for each patient of a group of patients experiencing ischemic symptoms at rest. In one embodiment Holter monitor ECGs are recorded for a median duration of 4 days to obtain 862 evaluable recordings for further analysis.

In a digital ECG recording, each heart beat is represented by a sequence of samples. The number of samples per beat depends upon the sampling rate of the ECG device and the length of the beat. For example, if the ECG is sampling at 128 Hz and the heart rate is 60 beats per minute, (i.e., one beat per second), then each beat will be represented by 128 samples. The numerical value of a particular sample corresponds to the height (or amplitude) of the ECG tracing at that time.

In one embodiment, for all patients with an evaluable recording, the continuous ECG signal from the first day is used for analysis and baseline noise removal was carried out by subtracting away a median filtered version of the original signal with a window of length 128 samples. Noise is further removed with wavelet denoising. Following segmentation, signal rejection is accomplished by the discarding of parts of the ECG signal that are found to either have a low signal quality index or where the standard deviation of the R wave amplitude is greater than a predefined threshold that is a function of the average height (or amplitude) of R-waves in the entire 24 hour ECG recording.

Specifically, noise removal is carried out in three steps. Baseline wander is first removed by subtracting an estimate of the wander obtained by median filtering the original ECG signal. The ECG signal is then filtered using wavelet denoising with a soft-threshold. Finally, sensitivity to calibration errors is decreased by normalizing the entire ECG signal by the mean R-wave amplitude.

Once the noise is removed, the physiological signal is segmented into components. For example, the ECG signal is segmented into heartbeats. Two QRS detection algorithms with different noise sensitivities are used to segment the signal. The first of these makes use of digital filtering and integration and has been shown to achieve a sensitivity of 99.69%, while the second is based on a length transform after filtering and has a sensitivity of 99.65%. Both techniques have a positive predictivity of 99.77%. QRS complexes are marked only at locations where these algorithms agree. These algorithms are provided as part of the public domain Physionet SQI package by PhysioNet, Massachusetts Institute of Technology, Cambridge, Mass.

Once the segmentation of the signal is complete, the signal undergoes a signal rejection process. While the noise removal steps help remove artifacts commonly encountered in long-term electrocardiographic records, the signal rejection process is designed to remove segments of the ECG signal where the signal-to-noise ratio is sufficiently low that meaningful analysis of the morphology is challenging even after noise removal. Such regions are typically dominated by artifacts unrelated to cardiac activity but that have similar spectral characteristics to the ECG signal, e.g., segments recorded during periods when there was substantial muscle artifact. This process is also used to remove beats representing cardiac activity that is not meaningful for subsequent processing, for example, for removing ectopic beats prior to computing morphological distances.

The process of signal rejection proceeds in two stages. Regions of the ECG signal with a low signal quality index are identified by combining four analytical methods: disagreement between multiple beat detection algorithms on a single ECG lead, disagreement between the same beat detection algorithm on different ECG leads, the kurtosis of a segment of ECG, and the ratio of power in the spectral distribution of a given ECG segment between 5-14 Hz and 5-50 Hz.

In one embodiment the Physionet SQI package implementation is used to automatically remove parts of the ECG signal with a low signal quality index from further analysis. The remaining signal data is divided into half hour windows, and the standard deviation of the R-waves during each half hour window is calculated. Any window with a standard deviation greater than 0.2887 is discarded. Given the earlier normalization of the ECG signal, under a conservative model that allows the R-wave amplitude to vary uniformly between 0.5 and 1.5 every beat (i.e., up to 50% of its mean amplitude), the standard deviation of the R-wave amplitudes is expected to be less than 0.2887 for any half hour window. This heuristic identifies windows that are likely corrupted by significant non-physiological additive noise, and where the morphology of the ECG cannot be meaningfully analyzed. In order to allow direct comparison with typical HRV analysis, prior to further analysis, the pre-ectopic, ectopic and post-ectopic beats are also removed. This removal is carried out in a fully automated manner using the beat classification algorithm present in the Physionet SQI package. The beat classification algorithm characterizes each beat by a number of features such as width, amplitude and RR interval, and then compares it to previously detected heartbeat types to assign it a label.

So, for example, in one study, to determine the predetermined standard deviation threshold, the mean and standard deviation of the R-wave height was computed over the 24 hour recording and Z-scores were then computed for each heartbeat. Heartbeats with Z-scores greater than 0.2887 (corresponding to the standard deviation of a uniform distribution where the lower and upper limits are 0.5-1.5) were discarded. Patients with less than 10 hours of clean data were excluded from the study (n=98). For the remaining 764 patients, ectopic and pre-ectopic beats were identified and removed Next the morphologic distance time series is derived. For every pair of consecutively occurring beats for a patient, a metric that describes morphologic differences between beats was applied. Differences in beat morphology are quantified by calculating the "energy difference" between beats.

Figure 3:
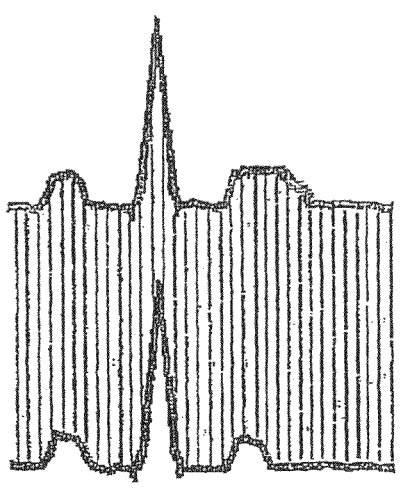
FIGS. 3 *a* and *b* are graphs comparing the ECGs of two adjacent heartbeats as determined by two different methods.
Figure 3:
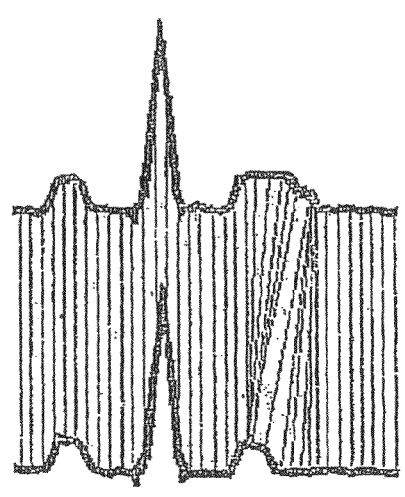

In one embodiment this energy difference is calculated by simply subtracting samples of one beat from another. However, if samples are compared based strictly on their distance from the start of the beat, one ends up computing the differences between samples associated with different waves or intervals. Consider the two heartbeats depicted in FIG. 3. In FIG. 3a samples are aligned based on their distance from the onset of the P-wave. One consequence of this is that samples that are part of the T-wave of the top heartbeat are compared with samples not associated with the T-wave of the bottom heartbeat. A measure computed this way will not reflect differences in the shapes of the T-waves of adjacent heartbeats.

A variant of a process called dynamic time-warping (DTW) is used to align samples that correspond to the same kind of underlying physiological activity. As depicted in the graphs shown in FIG. 3b this can require aligning a single sample in one heartbeat with multiple samples in another heartbeat. This variant process, termed physiological dynamic time-warping (PDTW), uses an algorithm with dynamic programming to search for an alignment that minimizes the overall distortion. Distortion is measured using a method that captures differences in both amplitude and time of ECG waves.

Once the heartbeats have been aligned, the cumulative energy difference between the heartbeats can be calculated. More precisely, given two heartbeats, $x_1$ and $x_2$, of length $l_1$ and $l_2$, respectively, the PDTW produces the optimal alignment of the two sequences by first constructing an $l_1$ by $l_2$ distance matrix. Each entry (i,j) in this matrix represents the square of the difference between samples $x_1(i)$ and $x_2(j)$. A particular alignment then corresponds to a path, $\phi$, through the distance matrix. The optimal alignment produced by PDTW minimizes the overall cost of the alignment path $\phi$.

The search for the optimal path is carried out in an efficient manner using dynamic programming. The final energy difference between the two heartbeats $x_1$ and $x_2$, is given by the cost of their optimal alignment, and depends on both the amplitude differences between the two signals, as well as the length K of the alignment (which increases if the two beats differ in their timing characteristics). In this way, the PDTW approach described here measures changes in morphology resulting from amplitude and timing differences between the two heartbeats. This approach transforms the original ECG signal from a sequence of beats to a sequence of energy differences. This new signal, comprising pairwise, time-aligned energy differences between beats, is the morphologic distance (MD) time series for that patient. The MD signal is then smoothed using a median filter of length 8 samples.

The PDTW used to align samples that correspond to the same underlying physiological activity is now described in more detail. As described above, the algorithm uses dynamic programming to search for an alignment that minimizes the overall distortion. All beats are zero padded to a consistent length before being compared with PTDW. Again, given two beats, $x_1$ and $x_2$, of length l, PDTW produces the optimal alignment of the two sequences by first constructing an l-by-l distance matrix d. Each entry (i,j) in this matrix d represents the square of the difference between samples $x_1[i]$ and $x_2[j]$. A particular alignment then corresponds to a path, $\phi$ through the distance matrix of the form:

$$\phi(k)=(\phi_1(k),\phi_2(k)), 1 \leq k \leq K \quad (1)$$

where $\phi_1$ and $\phi_2$ represent row and column indices into the distance matrix, and K is the alignment length. Any feasible path must obey the endpoint constraints:

$$\phi_1(1)=\phi_2(1)=1 \quad (2)$$

$$\phi_1(K)=l \quad (3a)$$

$$\phi_2(K)=l \quad (3b)$$

as well as the continuity and monotonicity conditions:

$$\phi_1(k+1) \leq \phi_1(k)+1 \quad (4a)$$

$$\phi_2(k+1) \leq \phi_2(k)+1 \quad (4b)$$

$$\phi_1(k+1) \geq \phi_1(k) \quad (5a)$$

$$\phi_2(k+1) \geq \phi_2(k) \quad (5b)$$

The optimal alignment produced by PDTW minimizes the overall cost:

$$C(x_1, x_2) = \min_{\varphi} C_\varphi(x_1, x_2) \quad (6)$$

where $C_\phi$ is the total cost of the alignment path $\phi$ and is defined as:

$$C_\varphi(x_1, x_2) = \sum_{k=1}^{K} d(x_1[\varphi_1(k)], x_2[\varphi_2(k)]) \quad (7)$$

The search for the optimal path is carried out in an efficient manner using a dynamic programming algorithm derived from the following recurrence for the cumulative path distance, $\gamma(i,j)$, and the distance matrix d:

$$\gamma(i, j) = d(i, j) + \min \begin{cases} \gamma(i-1, j-1) \\ \gamma(i-1, j) \\ \gamma(i, j-) \end{cases} \quad (8)$$

The final energy difference between the two beats $x_1$ and $x_2$, is given by the cost of their optimal alignment, which depends on the amplitude differences between the two signals and the length, K, of the alignment (which increases if the two signals differ in their timing characteristics). In a typical formulation of DTW, this difference is divided by K to remove the dependence of the cost on the length of the original observations. A problem with applying this correction in this context is that some paths are long not because the segments to be aligned are long, but rather because the observations are time-warped differently. In these cases, dividing by K is inappropriate since a difference in the length of a beats (or of parts of beats) often provides diagnostic information that is complimentary to the information provided by the morphology. Consequently, in this algorithm the division by K is omitted.

Figure 4:
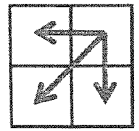
FIGS. 4*a* and *b* are representations of the recurrence relation of traditional (a) and physiologic dynamic time warping (b)
Figure 4:
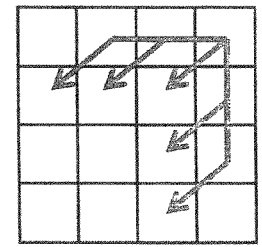

A further modification to traditional DTW in the PDTW is that the local range of the alignment path is restricted in the vicinity of a point to prevent biologically implausible alignments of large parts of one beat with small parts of another. For example, for an entry (i,j) in the distance matrix d, the only allowed valid paths pass through (i−1, j−1), (i−1, j−2), (i−2, j−1), (i−1, j−3) and (i−3, j−1). This is an adaptation of the Type III and Type IV local continuity constraints and ensures that there are no long horizontal or vertical edges along the optimal path through the distance matrix, corresponding to a large number of different samples in one beat being aligned with a single sample in the other. This leads to the following recurrence relation (which is also shown graphically in FIG. 4):

$$\gamma(i, j) = d(i, j) + \min \begin{cases} \gamma(i-1, j-1) \\ d(i-1, j) + \gamma(i-2, j-1) \\ d(i-1, j) + d(i-2, j) + \gamma(i-3, j-1) \\ d(i, j-1) + \gamma(i-1, j-2) \\ d(i, j-1) + d(i, j-2) + \gamma(i-1, j-3) \end{cases} \quad (9)$$

The process described above transforms the original ECG signal from a sequence of heartbeats into a sequence of energy differences. The resulting time-series is called the morphologic distance (MD) time-series for the patient. In one embodiment, this new signal, comprising pair-wise, time-aligned energy differences between beats, is then smoothed using a median filter of length 8. The median filtering process addresses noisy and ectopic heart beats that may have passed through the earlier preprocessing stage and lead to high morphologic distances. The smoothing process is geared towards ensuring that high levels of variability in the MD time-series correspond to locally persistent morphology changes, i.e., sustained differences in beat-to-beat morphology. In another embodiment no smoothing is done.

In some embodiments, the morphologic variability (MV) for the patient is subsequently calculated from the MD time series using metrics similar to those employed in other analyses of ECG signals. HRV, for example, uses a time series consisting of pairwise differences between successive RR intervals to calculate quantitative measures of variability in the heart rate. HRV measures include SDNN (the standard deviation of the time series), SDANAI (the standard deviation of the average of five minute windows of the time series) and HRV LF/HF (the average ratio of the power in the frequency spectrum of five minute windows of the time series between 0.04-0.15 Hz and 0.15-0.4 Hz). In some embodiments similar measures using the MD time series are computed, yielding three distinct MV measures, MV-SDNN, MV-SDANN and MV-LF/HF.

In a study upon which this invention was tested, high levels of variability in the MD time series were evaluated for association with the risk of death of the patients in the study. Patients were dichotomized into quintiles using the 80th percentile for the SDNN and SDANN measures, where high values corresponded to high morphologic variability. The MV-LF/HF measure, however, was dichotomized using the 20th percentile because low values of MV-LF/HF corresponded to high morphologic variability due to the contribution from the high frequency power in denominator term.

Although similar metrics are used to compare HRV and MV measures (e.g., SDNN, SDANN, LF/HF), it is important to note that MV measures differences in shape across entire heartbeats and is therefore more general than HRV. Differences in length contribute to MV, but are not the primary factor. For example although there may be subtle variations in the R-R interval, little change may be present in the morphology (e.g., shape) of the associated heartbeats (P-wave to T-wave). Conversely an ECG with subtle R-R wave variations may have more pronounced variation in the beat morphology. Such differences demonstrate that MV and HRV are different measures that capture distinct features of an ECG signal.

In the study, a statistical analysis of the hazard ratios (HRs) and 95% confidence interval (CIs) were estimated by using a Cox proportional hazards regression model. All available risk predictors were included in a univariate analysis of the outcome of death and myocardial infarction. Multivariable models were developed through two separate approaches, using variables demonstrating an association with outcomes on univariate analysis (P<0.10), and by stepwise backward elimination. Event rates were presented as Kaplan-Meier failure rates at 90 days. To estimate the discriminative value of MV, the area under the receiver operating characteristic curve (ROC) for the predicted survival of subjects was calculated.

MV quantifies differences in the shape of successive heartbeats in an ECG signal, where a heartbeat includes the entire P-wave-to-T-wave span. Therefore, while HRV focuses only on changes in the timing between different R-R time intervals, MV is much more general than HRV in that it focuses on mV amplitude changes in the shape of successive ECG heartbeats.

Each of the patients of the study had baseline risk factors and past cardiac history typical of patients with Non-ST-Segment Elevation Acute Coronary Syndrome (NSTEACS). Over sixty percent had an index diagnosis of non-ST-segment myocardial infarction due to an elevated biomarker of necrosis and half had new ST depression on the qualifying ECG.

The results of the univariate association between the clinical characteristics, ECG parameters and the patient outcomes are shown in Table 1. Of the clinical characteristics of the patients, only age and diabetes were significantly associated with death in this cohort. Of the ECG parameters, patients who had electrocardiographic evidence of ischemia within the first 24 hours after presentation had an increased risk of death (HR 4.56, 95% CI 1.02–20.41, p=0.047) but not MI (Table 2). With regard to the HRV measures, HRV-SDANN was the only measure associated with death as shown in Table 2 (HR 2.88, 95% CI 1.03-8.10, p=0.045). HRV-LF/HF was not associated with either death or MI and none of the HRV measures were associated with MI.

MV-LF/HF was significantly associated with death (Table 1), but none of the MV measures examined in this study was associated with subsequent MI. The rate of death was 4.7% in the lowest quintile compared to 2.1%, 1.1%, 2.2% and 0% in each subsequent quintile (log rank p=0.01). Patients with the lowest quintile of MV-LF/HF, which signifies greater morphologic variability, were also at significantly increased risk of death (HR 4.81, 95% CI 1.75-13.28, p=0.002). Moreover, almost half the deaths during follow-up corresponded to the lowest quintile of MV-LF/HF. There are no deaths in the highest quintile of MV-LF/HF (7 versus 0 deaths). The relationship with death was even more marked in the lowest decile (I-IR 6.53, 95% CI 2.32–18.34, p=0.001).

Figure 5:
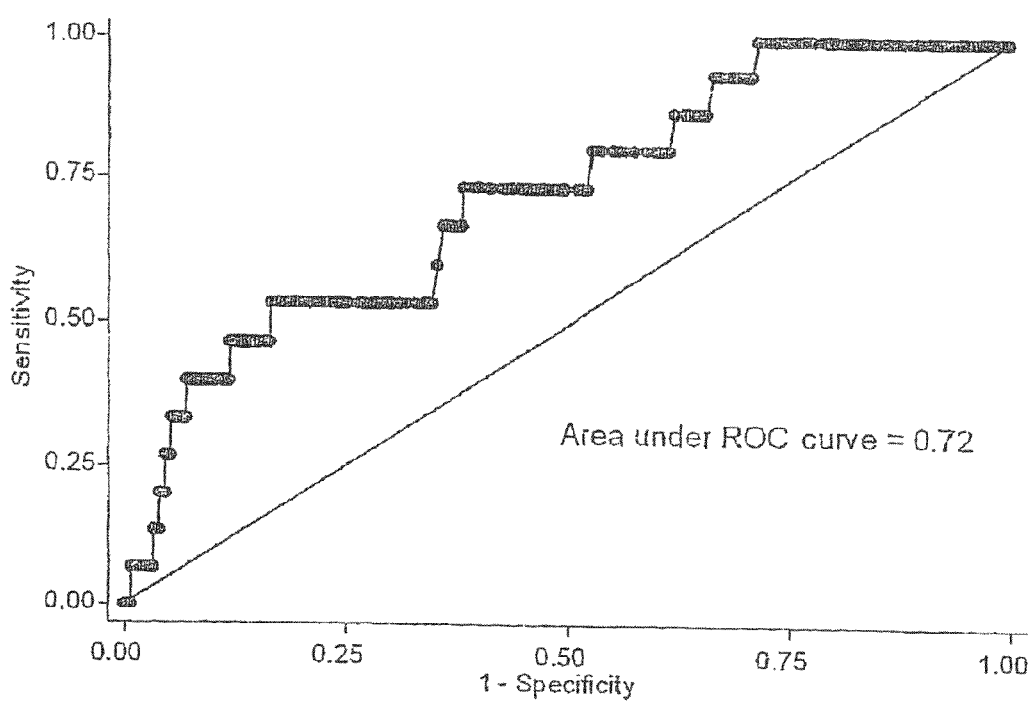
FIG. 5 is a graph of the receiver operating characteristic curve for MV-LF/HF as determined in a study.

The Receiver Operating Characteristic (ROC) curve and corresponding C-statistic, for MV LF/HF and the outcome of death are presented in FIG. 5. MV-LF/HF has a C-statistic of 0.72. For comparison, the C-statistic for HRV-SDANN for this cohort is 0.56.

Lastly, to test. whether an analysis of the entire heartbeat, as opposed to a particular segment of the ECG signal, is important for achieving these results, the contribution of each segment of the ECG signal (e.g., ST segment or QT interval) to the overall MV-LF/HF value was analyzed and no one segment was found to be predominant in its overall effect on MV-LF/HF. In short, the entire signal is needed to obtain the results found.

Patients with low values of MV-LF/HF remained at a significantly elevated risk of death even after controlling for baseline characteristics. In multivariable analyses, a low MV-LF/HF was consistently associated with death, regardless if the model was built with all unvariate variables associated with death at p<0.1 (adjusted HR. for lowest quintile 4.10, p=0.009) or with a stepwise backward elimination method (adjusted MZ 3.75, p=0.014)-(Table 3). To determine the contribution of HRV to this association, HRV-SDANN was explicitly included in all models, regardless of its p-value in the univariate analysis. However, HRV-SDANN was not independently associated with outcomes in either model.

Figure 6:
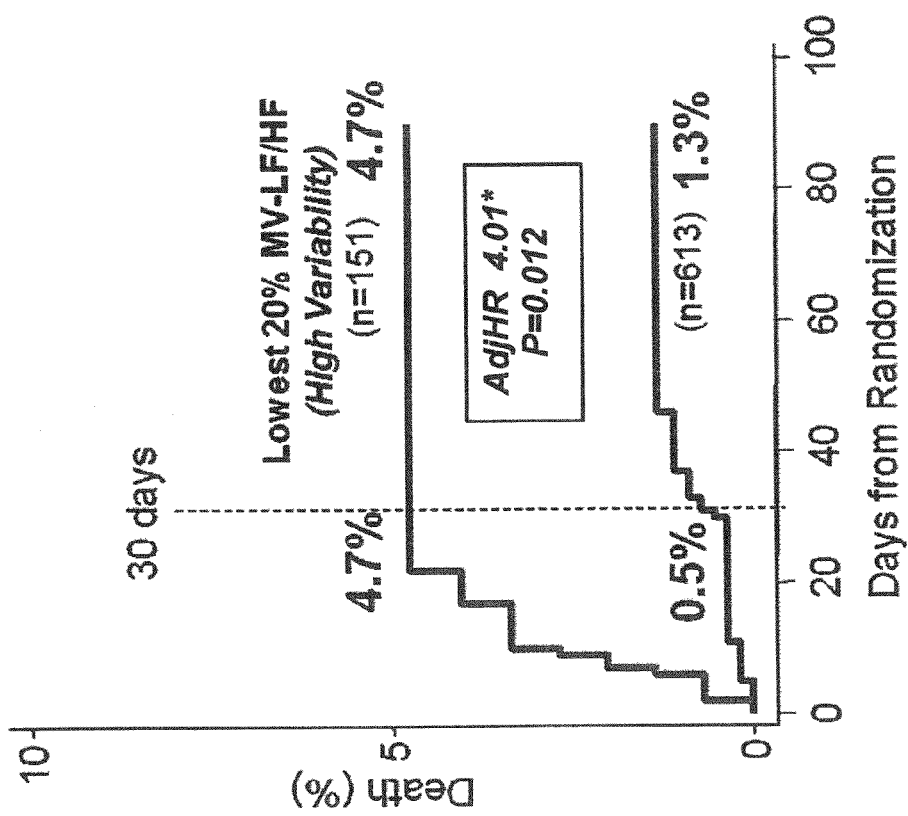
FIG. 6 is a set of Kaplan-Meier mortality curves in the high and low risk populations for patients in a study according MV-LF/HF.

Kaplan-Meier mortality curves for patients in the high and low risk populations according MV-LF/HF are shown in FIG. 6. Patients with the lowest quintile of MV-LF/HF during the first 24 hours after study entry were at significantly elevated risk of death over the subsequent 90 days, with the difference apparent within the first thirty days. Moreover, the association between MV and death was consistent in several subgroups, including the elderly, women, patients with ST depression on admission and patients without episodes of ischemia as detected on ECG.

Thus the ECG remains critical in the diagnosis and prognostication of patients with cardiovascular disease. Myocardial ischemia, for example, is commonly diagnosed from dynamic changes within the ST-T wave segment. There are data, however, which suggest that ischemia may be associated with subtle morphologic changes throughout the entire ECG signal that are not commonly appreciated in clinical practice. Moreover, even in the absence of overt signs of ischemia, subtle ECG changes may indicate electrochemical abnormalities within the myocardium that are potentially proarrhythmic.

An automated procedure for identifying subtle morphologic changes between successive heartbeats in a surface ECG signal would therefore provide additional data that could be used to identify patients at high risk following ACS. MV-based measures do exist that have a significant association with myocardial infarction/ischemia. This study demonstrated that a low MV-LF/HF ratio is significantly, and independently, associated with an increased risk of death in the subsequent 90 days following hospital admission for NSTEACS. The increased hazard for death associated with low MV-LF/HF is especially apparent within the first 30 days after hospitalization and is consistent among many different subgroups including patients with no evidence for ischemia on the ECG. In addition, MV-LF/HF has a C-statistic of 0.72, suggesting that MV-LF/HF provides a reasonable measure that can be used to discriminate between low-risk and high-risk patients post NSTEACS. Thus, MV-LF/HF may be a useful measure for short-term risk stratification in patients admitted with ACS.

In addition to the diagnosis of disease states, morphologic variability can be used to follow the effects of various drugs and procedures on a physiological system. For example in one study the administration of the anti-anginal/anti-arrhythmic drug Ranolazine was shown to lower the MV, but not the HRV.

Additionally, MV can be combined with other measures of clinical significance such as a TIMI and/or GRACE risk score to improve outcome prediction. One study which considered both the TIMI risk score and MV found that while patients in the TIMI risk group 1 (TRG1) were predicted to have a low risk of death, their predicted risk accurately increased when the TIMI score was combined with MV. In addition, other clinical measurements such as imaging, biomarkers, and clinical characteristics can be combined with MV to improve outcome prediction.

The MV-LF/HF measure discussed above is intended to be analogous to the HRV-LF/HF measure so that the utility of using the MD time series in place of other time series could be fairly evaluated. The frequency bands for the low frequency (0.04 Hz-0.15 Hz) and high frequency components (0.15 Hz-0.40 Hz) are those typically used for HRV. The LF and HF frequency bands are associated with the timescales on which the sympathetic nervous system and vagal activity regulate heart rate. Since morphologic variability is intended to be a measure of a different phenomenon, i.e., electrical instability of the myocardium, there is little reason to believe that the frequency bands used for HRV would also be optimal for risk assessment with MV. There is in fact a range of better frequencies for the purposes of MV-based risk stratification. This is referred to as the diagnostic frequency or (DF) band.

Figure 7A:
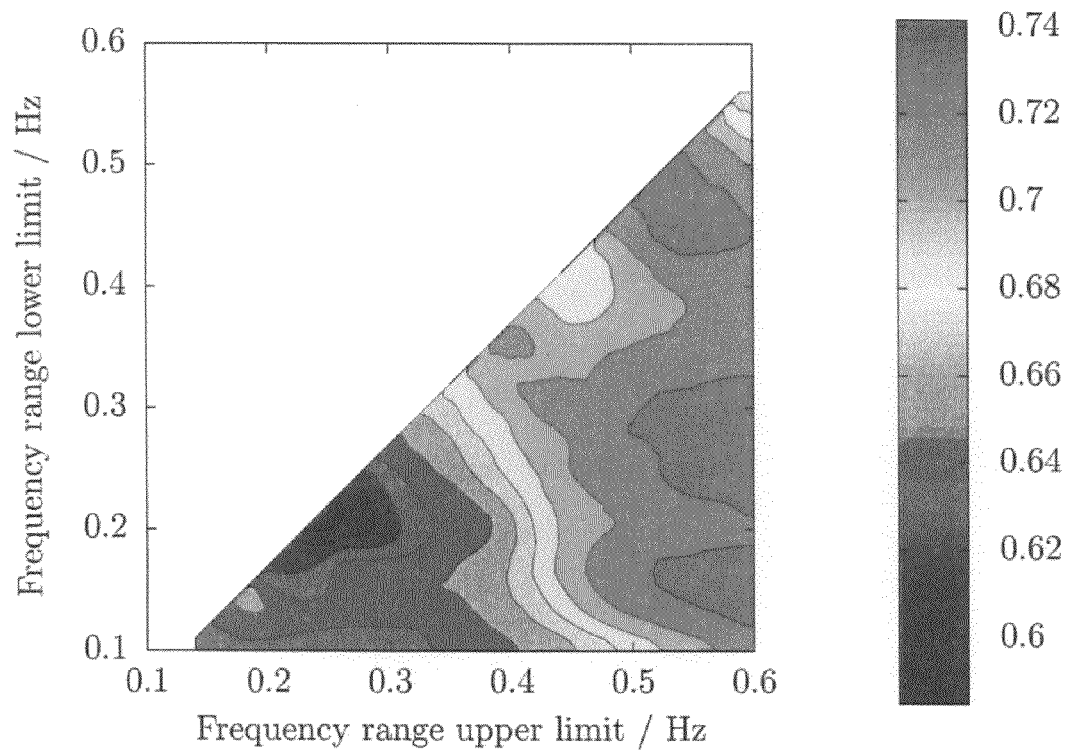
FIGS. 7 *a* and *b* are accuracy—frequency graphs used to determine a diagnostic frequency according to one embodiment of the invention.
Figure 7B:
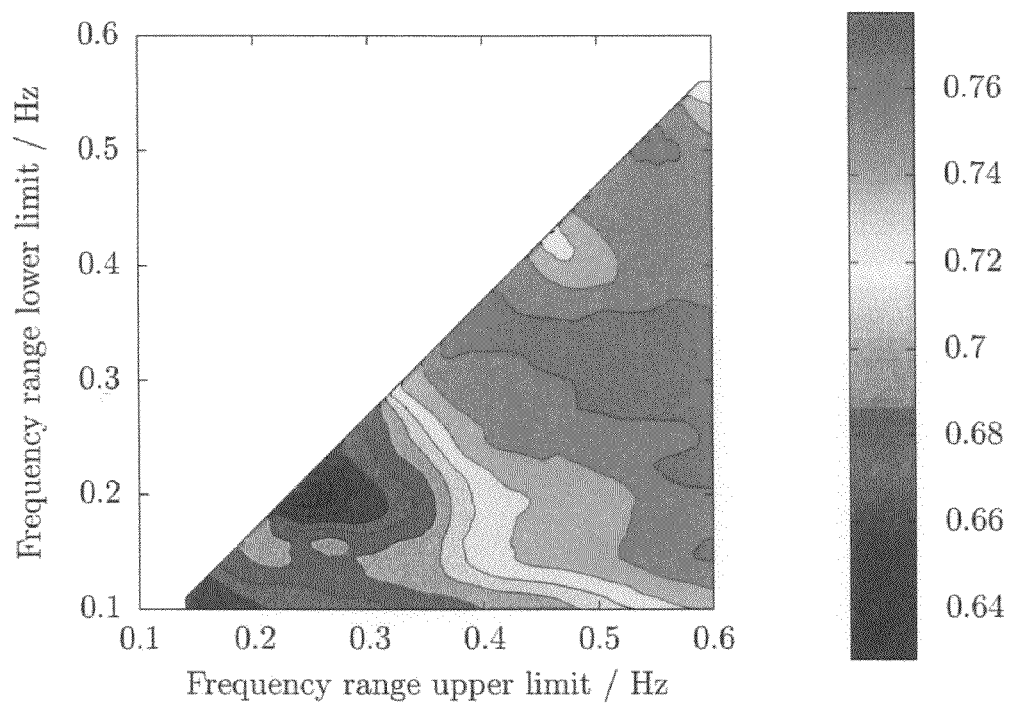

To identify the DF band, all possible frequency bands within the, range 0.1 Hz-0.6 Hz were evaluated to identify an optimal band. Frequency bands with a width less than 0.05 Hz were excluded to ensure that the energy within the band could be estimated robustly from the time series data. Based on the results shown in FIGS. 7a and b, the DF band is determined to be 0.30 Hz-0.55 Hz. This frequency range is a good predictor of death within 90 days. The risk measure obtained by using the DF band is termed the MV-DF measure. The risk of death as MV-DF increases shows a: graded response. However, although low MV-LF/HF is significantly associated with risk of MI there was no significant association between high MV-DF and MI.

Morphologic variability identifies unstable heartbeat-to-heartbeat variations in the cardiac conduction path that portend high risk for fatal arrhythmias. A diagnostic frequency (DF) band associated with the characteristic timescales of such variation exists such that high DF energy in this band is strongly associated with risk of death. ECGs having a small fraction (10%) of extremely high-MV activity predicts a high risk for death, even more so than having merely generally high MV. Not only does the MV-DF metric outperform the MV-LF/HF metric, it has the added advantage of having a. simpler characterization, since it only relies on the energy in one frequency band rather than two. A preliminary investigation showed that using a two-band MV-LF/HF-like metric is unlikely to yield significantly better risk stratification.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

In another aspect, the invention relates to another method of extracting information from physiological signals and analyzing that extracted data to predict patient outcomes and responses. Although this will be generally described in terms of analyzing large amounts of cardiovascular data, many other types and quantities of physiological data may be analyzed in this manner.

The notion of representing physiological signals as symbolic sequences follows from the possibility of meaningfully segmenting many important signals. For example, data from the heart and lungs often comprises units such as heart beats or breaths. Other data, such as EEG, can be segmented based upon units of time. It is often more natural to analyze physiological signals in terms of these units than at the level of raw samples. Moreover, many of these units, while differing in the samples that comprise them, represent the same or similar physiological activity. By replacing the samples representing such units by a single symbol, a significant level of abstraction is achieved. In doing so, the underlying repetitive structure and redundancy is exploited to obtain a layer of data reduction. The raw physiological data is re-expressed to retain salient differences between units of activity while abstracting away the common structure. For example, raw ECG data can be partitioned at the level of heart beats into different equivalence classes, each of which is assigned a unique symbol for identification. This reduces the data rate from around 4,000 bits/second (for a beat lasting one second in a signal sampled at 360 Hz with 11 bit quantization) to n bits/second (where n depends upon the number of bits needed to differentiate between symbols).

The data reduction introduced by symbolization reduces the search space for the detection of interesting activity and provides a significant computational advantage over working in the original space of the raw signal. A further advantage of using symbolization is that it implicitly abstracts away some of the time-normalization issues that complicate the use of cross-correlation and other techniques that operate on raw time samples.

In brief overview, the process begins with the acquisition of a physiological signal. To abstract continuous waveforms into a string representation that can be mined for patterns more efficiently, the original signal is segmented into units, the units are then partitioned into classes and then a label is assigned to each class. This effectively reduces the original data into a sequence of symbols. For example, if the signal is an ECG signal, the ECG signal is partitioned into heartbeats. The signals need not be periodic or quasiperiodic to be segmented. A signal, for example, can be segmented based on some outside reference such as a time scale. Once the signal is segmented, the components are grouped or mapped into a plurality of information classes using morphological features. A unique symbol is assigned to each information class. This allows the original signal to be re-expressed as a symbolic sequence, corresponding to the sequence of labels assigned to the underlying components. The symbolic sequence is then examined for clinical significance. In one embodiment, a representative component for each class may be assigned and displayed if the clinician wishes to see what an underlying waveform looks like.

In one embodiment the segmentation stage decomposes the continuous input signal into intervals with biologically relevant boundaries. A natural approach to achieve this is to segment the physiological signals according to some well-defined criteria. For example, in various embodiments, the R-R intervals for heart beats in the case of an ECG signal and peaks of inspiration and expiration in the case of respiratory cycle data are used. Further, since most cardiovascular signals are quasiperiodic, cyclostationarity is exploited for data segmentation of an ECG.

In one embodiment the task of partitioning is treated as a data clustering problem. Roughly speaking, the goal is to partition the set of segments into the smallest number of clusters such that each segment within a cluster represents the same underlying physiological activity. For example, in the case of ECG data, one cluster might contain only ventricular heartbeats (i.e., heartbeats arising from the ventricular cavities in the heart) and another segment might only contain junctional heartbeats (i.e. heartbeats arising from a region of the heart called the atrioventricular junction). Each of these heartbeats has different morphological characteristics that cause them to be placed in different clusters. The centroid of the cluster may be the representative member of the class.

Broadly speaking, there are two approaches to decide when to terminate the iterative clustering process. The simplest approach is to terminate at the iteration when the clustering process has produced a predetermined number of clusters. However, in the case where there are no prior assumptions about the appropriate number of clusters a more complex approach is used in which the number of clusters is determined by the dataset itself. Once the clusters are formed they are labeled.

There is a set of generally accepted labels that cardiologists use to differentiate the distinct kinds of heartbeats. Although cardiologists occasionally disagree about what label should be applied to some heartbeats, labels supplied by cardiologists provide a useful way to check whether or not the heartbeats in a cluster represent the same underlying physiological activity. However, in many cases finer distinctions can be more clinically relevant than is apparent from these labels. Normal heartbeats, for example, are usually defined as heartbeats that have morphologic characteristics that fall within a relatively broad range; e.g., QRS complex less than 120 ms and PR interval less than 200 ms.

Nevertheless, it may be clinically useful to further divide "normal" beats into multiple classes since some normal beats have subtle morphological features that are associated with clinically relevant states. One example of this phenomenon is Wolff-Parkinson-White (WPW) syndrome. In this disorder, patients have ECG beats that appear grossly normal, yet on close inspection, their QRS complexes contain a subtle deflection called a δ-wave and a short PR interval. Since such patients are predisposed to arrhythmias; the identification of this electrocardiographic finding is of interest. For reasons such as this, standard labels cannot simply be used to check whether or not an appropriate number of clusters have been found. Once the clusters have been determined and labeled, the resulting symbolic strings are examined for patterns.

Considering the process in more detail, the process first extracts features from each segment by sampling the continuous data stream at discrete points, and then groups the segments based upon the similarity of their features. Many automated techniques exist for the unsupervised partitioning of a collection of individual observations into characteristic classes.

In one embodiment clustering methods are utilized for partitioning the signal. In one embodiment Max-Min clustering is used to separate segmented units of cardiovascular signals into groups. This form of clustering proceeds in a greedy manner; identifying a new group, at each iteration, that is maximally separated from other existing groups.

In one embodiment physiological dynamic time-warping (PDTW), discussed above, is used to calculate the time-normalized distance between each pair of observations. Central to the clustering process is the method used to measure the distance between two segments. For physiological signals, this is complicated by the differences in lengths of segments. Physiological dynamic time-warping allows subsignals to be variably dilated or shrunk.

The Max-Min clustering used proceeds by choosing an observation at random as the first centroid, c1, and setting the set S of centroids to {c1}. During the i-th iteration, (ci) is chosen such that it maximizes the minimum distance between (ci) and observations in S:

$$c_i = \arg\max_{x \notin S} \min_{y \in S} C(x, y) \qquad (10)$$

where $C(x,y)$ is defined as in (6). The set S is incremented at the end of each iteration such that S is the union of S and $c_i$.

The number of clusters discovered by Max-Min clustering is chosen by iterating until the maximized minimum dissimilarity measure falls below a specified threshold θ. Therefore the number of clusters, k, depends on the separability of the underlying data to be clustered.

The time to make the calculations can be reduced by exploiting the fact that in many cases two observations may be sufficiently similar that it is not necessary to calculate the optimal alignment between them. A preliminary processing block that identifies (c) such homogenous groups from N observations without alignment of time-samples will reduce the number of PDTW comparisons. This pre-clustering can be achieved in a computationally inexpensive manner through an initial round of Max-Min clustering using a simple distance metric.

Figure 8:
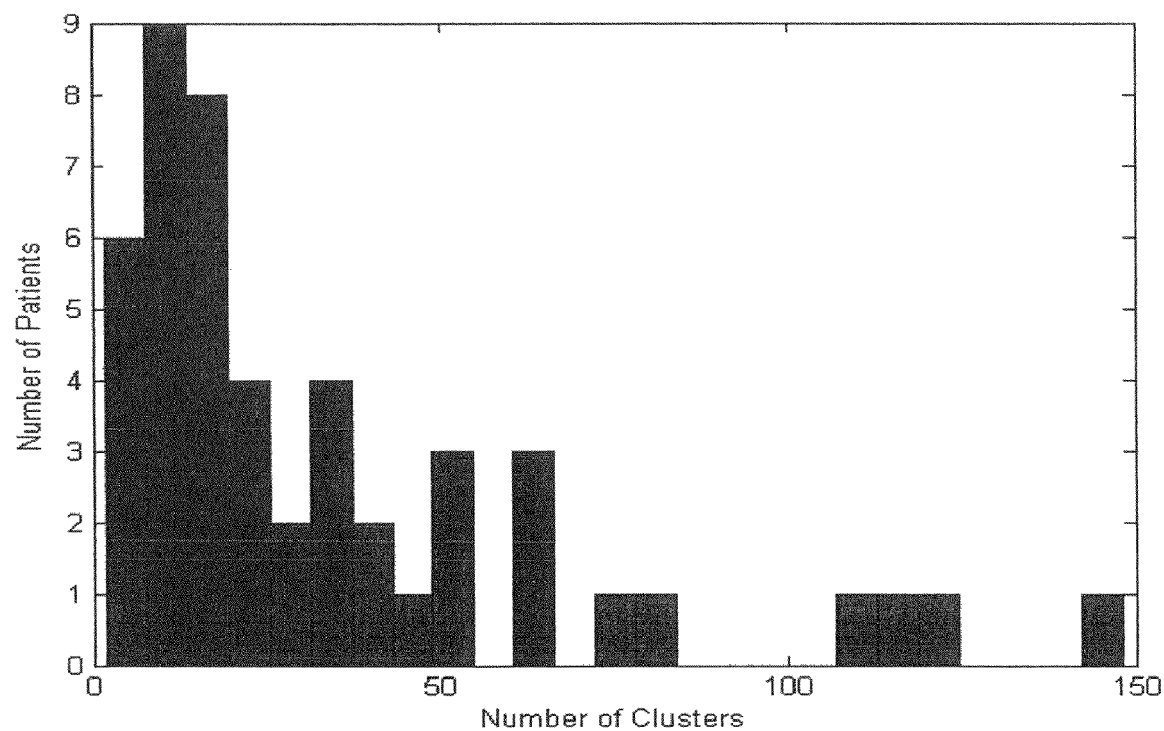
FIG. 8 is a histogram of the number of clusters formed per patient in a study using one embodiment of the invention.

The process was applied to electrocardiographic data in the Physionet MIT-BIH Arrhythmia database, which contains excerpts of two-channel ECG sampled at 360 Hz per channel with 11-bit resolution. The activity recorded in the database is hand-annotated by cardiologists, allowed the results of the present method to be validated against human specialists. In the tests, for each patient in the database, different classes of ECG activity between consecutive R waves within each QRS complex were searched. A Max-Min threshold of $\theta=50$ was used, with this value being chosen experimentally to produce a small number of clusters, while generally separating out clinical classes of activity for each patient. A histogram for the number of clusters found automatically for each patient is provided in FIG. 8. The median number of clusters per patient was 22. For the median patient, 2202 distinct beats were partitioned into 22 classes. A relatively large number of clusters were found in some cases. These problematic files are described in the MIT-BIH Arrhythmia database as being difficult to analyze owing to considerable high-grade baseline noise and muscle artifact noise. This leads to highly dissimilar beats, and also makes the ECG signals difficult to segment.

There are a number of ways to compare a clustering produced by the present algorithm (CA) to the implicit clustering which is defined by cardiologist supplied labels (CL). CA and CL are said to be isomorphic if for every pair of beats, the beats are in the same cluster in CA if and only if they are in the same cluster in CL. If CA and CL are isomorphic, the present algorithm has duplicated the clustering provided by cardiologists. In most cases CA and CL will not be isomorphic because the present algorithm typically produces more clusters than are traditionally defined by cardiologists. This is an advantage of the approach because it enables the method to identify new morphologies and patterns that may be of clinical interest.

Alternatively, CA is consistent with CL if an isomorphism between the two can be created by merging clusters in CA. For example, two beats in an ECG data stream may have abnormally long lengths and therefore represent "wide-complex" beats. However, if they have sufficiently different morphologies, they will be placed in different clusters. The creation of an isomorphism between CA and CL can be facilitated by merging all clusters in CA which consists of wide-complex beats. While consistency is a useful property, it is not sufficient. For example, if every cluster in CA contained exactly one beat, it would be consistent with CL.

To determine whether the algorithm generates a clustering that is consistent with cardiologists supplied labels, the labels of beats in each cluster were examined and the cluster assigned a label corresponding to its majority element. For example, a cluster containing 1381 normal beats, and 2 atrial premature beats would be labeled as being normal. Beats in the original signal were then assigned the labels of their clusters (e.g., the 2 atrial beats in the above example would be labeled as normal). Finally, the differences between the labels generated by this process and the cardiologist supplied labels in the database were tabulated. This procedure identifies, and effectively merges, clusters that contain similar types of beats.

For the purposes of testing, only classes of activity that occurred in at least 5% of the patients in the population, i.e., 3 or more patients in the MIT-BIH Arrhythmia database were considered. Specifically, even though the presence of atrial escape beats in one patient in the MIT-BIH Arrhythmia database and ventricular escape beats in another patient in the database were detected, these results were not reported in the subsequent discussion since no other patients in the population had atrial or ventricular escape activity and it is hard to generalize from performance on a single individual. During the evaluation process, labels that occur fewer than three times in the original labeling for a patient (i.e., less than 0.1% of the time) were also ignored.

Tables 1 and 2 show the result of this testing process. Differences between the labeling generated by the present process and the cardiologist supplied labels appearing in the database do not necessarily represent errors. Visual inspection of these differences by a board-certified cardiologist, who was not involved in the initial labeling of beats in the Physionet MIT-BIH Arrhythmia database, indicates that experts can disagree on the appropriate labeling of many of the heartbeats where the classification differed. Nevertheless, for simplicity these "differences" are referred to as "errors."

In Table 4, for the purpose of compactly presenting results, the clinical activity is grouped as follows:

Normal

Atrial (atrial premature beats, aberrated atrial premature beats and atrial ectopic beats)

Ventricular (premature ventricular contractions, ventricular ectopic beats and fusion of normal and ventricular beats)

Bundle branch block (left and right bundle branch block beats)

Junctional (premature junctional beats and junctional escape beats)

Others

The overall misclassification percentage in these cases is approximately 1.4%. In the majority of the patients, there is less than 1% error. As Tables 1 and 2 indicate, the symbolization technique does a reasonably good job both at identifying clinically relevant clusters and at assigning individual beats to the appropriate cluster.

The data in the first row of Table 5 sheds light on critical errors; i.e. errors that cause one to conclude that a patient does not exhibit a certain type of heartbeat when in fact, their ECG signal does contain a significant number of the beats in question. More precisely, a critical error is deemed to have occurred when a patient has at least three instances of a clinically relevant type of heartbeat and there does not exist at least one cluster in which that beat is a majority element.

For example, for each patient for whom the cardiologists found three or more "premature ventricular complexes," the algorithm formed a cluster for heartbeats of that type. On the other hand, for one quarter of the patients with at least three "fusion of ventricular and normal heartbeats," the algorithm did not form a cluster for that type of heartbeat.

In 43 out of 48 patients there were no critical errors. This is important because, in the presence of critical errors, an inspection of the data through visualization of the cluster representatives would conceal the presence of some activity in the dataset. Avoiding critical errors is a challenge because for some patients, the number of elements in different clinical classes varies by a few orders of magnitude. For example for one patient, the process correctly identified the three atrial premature beats amidst the 1852 normal beats. For some classes of activity, however, morphology-based clustering generated labels different from those provided by the cardiologists.

Figure 9A:
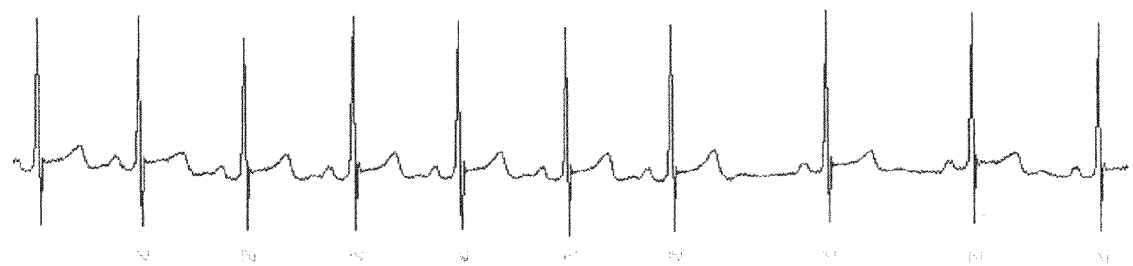
FIGS. 9 *a* and *b* are ECG tracings of a patient with normal heartbeat shape.
Figure 9B:
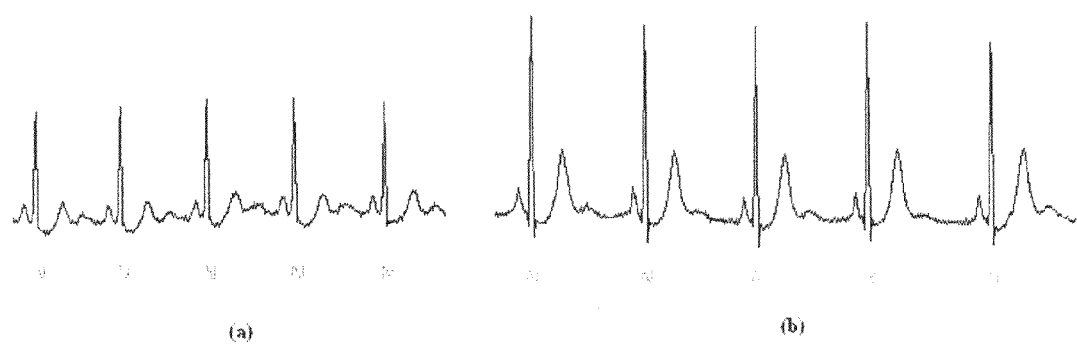

Sometimes the algorithm placed heartbeats for which cardiologists have supplied the same label into different clusters. As was discussed above, this is not necessarily a bad thing as subtle distinctions between "normal" beats may contain useful clinical information. FIGS. 9a and b present instances in which the algorithm separated beats that were assigned the same label by cardiologists. In FIG. 9a, morphology-based analysis is able to distinguish changes in length. In FIG. 9b, changes in amplitude are discerned automatically. These morphological differences may represent clinically important distinctions. In each instance, heartbeats which are classified as "normal" have very different morphologic features that may be associated with important disease states. Abrupt changes in the R-R interval, like that noted in FIG. 9a, correspond to rapid fluctuations in the heart—a finding which can be associated with a number of clinically important conditions such as Sick Sinus Syndrome (SSS) or sinus arrhythmia. Similarly, significant changes in QRS amplitude, like that seen in FIG. 9b, can be observed in patients with large pericardial effusions. Both of these diagnoses are important syndromes that can be associated with adverse clinical outcomes.

Data from the MIT-BIH Arrhythmia database were used during the initial design of the symbolization algorithm, and the results reported in Tables 1 and 2 were generated on this data set. To test the robustness of the method, the algorithm was also tested on ECG data on the first forty patients from the MGH/MF Waveform database which was not used in design of the algorithm. This dataset contains fewer episodes of interesting arrhythmic activity than the MIT-BIH Arrhythmia database and is also relatively noisy, but contains ECG signals sampled at the same rate (i.e., 360 Hz) with 12 bit resolution; i.e., a sampling rate and resolution similar to that of the MIT-BIH Arrhythmia database. The recordings are also typically an hour long instead of 30 minutes for the MIT-BIH Arrhythmia database. Table 6 shows the performance of the symbolization algorithm on this dataset. The results are comparable to the ones obtained for the MIT-BIH Arrhythmia dataset. The median number of clusters found in this case was 43.

Symbolization leads to a discrete representation of the original cardiovascular signals. The goal of this analysis is to develop techniques that operate on these symbolic data to discover subsequences that correspond to clinically relevant activity in the original signal. A key aspect of the approach is that no domain expertise is used to identify sub-sequences in the original data stream.

Since the intent is to apply these techniques to massive data sets, computational efficiency is an important consideration. The techniques also need to operate robustly on noisy symbolic signals. There are two important sources of noise: noisy sensors and imperfections in the symbolization process that assign distinct symbols to beats that should have been assigned the same symbol.

A sequence w1w2 . . . wH constitutes an exact or perfect repeat in a symbolic signal v1v2 . . . vN with L>1 periods if for some starting position s:

$$v_s v_{s+1} \ldots v_{s+HL-1} = (w_1 w_2 \ldots w_H)^L \quad (11)$$

The number of repeating periods L can be chosen to trim the set of candidate repeats. Rhythms are defined as repeating subsequences in a symbolic signal. To address the issue of noise, equation 11 is generalized to approximate repeats, which allow for mismatches between adjacent repeats. A sequence w1w2 . . . wH is an approximate repeat with L periods if there exists a set of strictly increasing positions s1, . . . , sL+1 such that for all $1 \leq i \leq L$:

$$\phi(w_1 w_2 \ldots w_H, v_{s_i} v_{s_i+1} \ldots v_{s_{i+1}-1}) \leq \gamma \quad (12)$$

where ϕ(p,q) represents a measure of the distance between sequences p and q (e.g., the Hamming distance) and γ is a threshold constraining the amount of dissimilarity allowed across the repeats. The final positions L+1 can be at most one more than the length of v1v2 . . . vN.

The mining of physiological signals for recurrent transient patterns can be mapped to the task of detecting statistically significant subsequences that occur with sufficient frequency. The challenge is to discover complexes w1w2 . . . wH with shared spatial arrangement that occur more frequently in the symbolic signal v1v2 . . . vN than would be expected given the background distribution over the symbols in the data. The ranking function for this criterion considers two factors: 1) the significance of a pattern relative to the background distribution of symbols; and 2) the absolute count of the number of times the pattern was observed in the data stream. Denoting the probability operator by Pr, the first criterion is equivalent to evaluating the expression:

$$\frac{Pr(w_1 w_2 \ldots w_H)}{\prod_{i=1}^{H} Pr(w_i)} \quad (13)$$

The second criterion is necessary to deal with situations where the pattern contains a very rare symbol. Depending on the length of the pattern, the probability ratio in (13) may be unduly large in such instances. Hence, the absolute number of times that the pattern occurs is explicitly considered. Exact patterns that occur with high frequency can be found by a linear traversal of v1v2 . . . vN while maintaining state to record the occurrence of each candidate pattern. In exact patterns can be handled by searching in the neighborhood of a candidate pattern in a manner similar to the use of the BLAST algorithm. An example of a clinical condition that can be detected by this approach is paroxysmal atrial tachycardia.

Short bursts of irregular activity can be detected by searching for episodes of increased entropy. The symbolic symbols were searched for subsequences in symbolic signals with an alphabet of size Λ in which the entropy approaches log 2Λ. An example of a clinical condition that can be detected by this approach is atrial fibrillation. Conversely, the absence of sufficient variation (e.g., changes in the length of heart beats arising due to natural fluctuations in the underlying heart rate) can be recognized by the lack of entropy over long timescales.

The presence of massive datasets also restricts visibility of multi-modal trends. Most humans are restricted in their ability to reason about relationships between more than two inputs. Automated systems can help address this limitation, but techniques to analyze raw time-series data are computationally intensive, particularly for signals with high sampling rates. Mutual information analysis cannot readily be applied to raw data, particularly in the presence of time-warping.

For example, one can examine the mutual information across M sequences of symbols by treating each sequence as a random variable Vi, for 1≦i≦M and examining the multivariate mutual information I(V1, . . . , VM):

$$\sum_{j=1}^{M} \sum_{\{i_1,\ldots,i_j\}\subseteq\{1,\ldots M\}} (-1)^{j+1} H(V_{i_1}, \ldots, V_{i_j}) \quad (14)$$

where H denotes the joint entropy between random variables. Computing I(V1, . . . , VM) in this manner is intractable for large values of M. For computational efficiency, it is possible to employ k-additive truncation, which neglects corrective or higher order terms of order greater than k.

An alternative formulation of the problem of detecting multi-modal trends involves assessing the degree of association of sequences in M with activity in a sequence not in M (denoted by VNEW). Consider a set of symbols Ui, each corresponding to a realization of the random variable Vi for 1≦i≦M. Let H(VτNEW) be the entropy in VNEW at all time instants t that are some specified time-lag, τ, away from each joint occurrence of the symbols Ui. I.e., H(VτNEW) measures the entropy in VNEW at all time instants t satisfying the predicate:

$$(V_1[t-\tau]=U_1) \land \ldots \land (V_M[t-\tau]=U_M) \quad (15)$$

The time-lagged association between the joint occurrence of the symbols Ui and signal VNEW is defined as:

$$H(V_{NEW}) - H(V^\tau_{NEW}) \quad (16)$$

If a time-lagged association exists, the entropy in VNEW at all time instants t that obey the predicate in (10) will be less than the entropy across the entire signal, i.e., activity at these time instants will be more predictable and consistent with the underlying event in signals V1 through VM.

The difference between the formulations described by equations (14) and (16) can be appreciated by considering two signals V1 and V2. Equation (14) essentially determines if the two are correlated. In (16), the focus is on identifying whether a specific class of activity in V1 is associated with a consistent event in V2, even if the signals may otherwise be uncorrelated. Searching for time-lagged associations using the method in (16) is likely to be important for discovering activity that is associated with clinical events. An example of a clinical condition that can be detected by this approach is pulsus paradoxus.

Automated methods can be used to discover complex rhythms that are easy for clinicians to miss. In one case, approximate repeat detection identifies an intricate pattern which likely represents episodes of an ectopic atrial rhythm with aberrant ventricular conduction superimposed on an underlying sinus rhythm. This clinically significant rhythm was not marked by the clinicians who annotated the signal.

An example in which the detection of recurrent transient patterns in symbolic signals reveals many short, unsustained episodes repeats is tachyarrhythmic activity. The tachyarrythmic beats occur infrequently relative to normal beats, and consecutive runs of such activity are unlikely to have occurred merely at random. The irregularity of activity leads to entropy increasing noticeably in windows of the symbolic stream, owing to the unstructured nature of the underlying disorder.

In addition to analyzing the symbolic sequences for a single patient over time, automated methods may be used to analyze signals from multiple patients. Given multiple observations of a common event across different patients, analysis of the symbolic sequences for these patients may be used to discover commonalities that are associated with the common event. The method searches for activity that occurs more often preceding the event than the background rate of occurrence indicates. These commonalities may have predictive value.

Our method identifies such predictive physiological patterns in the absence of prior knowledge. It uses the principle of conservation to identify activity that consistently precedes an outcome in patients, and incorporate a novel process to efficiently search for such patterns in large datasets.

The method of identifying conserved activity that is unlikely to have occurred purely by chance in symbolic data is analogous to the discovery of regulatory motifs in genomic datasets. The present method builds upon existing work in this area, generalizing the notion of a regulatory motif and enhancing current techniques to operate robustly on non-genomic data. It also addresses two significant considerations associated with motif discovery in general, i.e., computational efficiency and robustness in the presence of degeneracy and noise. The method uses the novel concept of active regions and novel subset-based techniques such as a two-layer Gibbs sampling algorithm.

A different method is used for the case where both positive and negative examples are available. In one embodiment, the method searches for activity that occurs significantly more often in the time period shortly before the event than in other time periods for the same patient. In another embodiment, the method searches for activity that occurs significantly more often in patients that suffer the event than in patients that do not.

A two-step process is used to discover such patterns. Using locality sensitive hashing (LSH), the method estimates the frequency of all subsequences and their approximate matches within a given Hamming radius in labeled examples. The discriminative ability of each pattern is then assessed from the estimated frequencies by concordance and rank sum testing.

The use of LSH to identify approximate matches for each candidate pattern helps reduce the runtime of our method. Space requirements are reduced by decomposing the search problem into an iterative method that uses a single LSH table in memory. Clustering with redundancy based on a 2-approximate solution of the k-center problem decreases the number of overlapping approximate groups while providing exhaustive coverage of the search space. Sequential statistical methods allow the search process to use data from only as many training examples as are needed to assess significance.

To reduce the computation time for this process, the method of Indyk and Motwani of locality sensitive hashing (LSH) is used as a randomized approximation algorithm to solve the nearest neighbor problem. Given a set of subsequences, the goal of LSH is to preprocess the data so that future queries searching for closest points under some $l_p$ norm can be answered efficiently.

Every subsequence is passed through the LSH data structure for matches with a hamming distance of at most d. This process is associated with considerable redundancy, as matches are sought individually for subsequences that are very similar. The overlap between approximate patterns increases the computational needs of the pattern discovery process and also makes it more challenging to interpret the results as good patterns may appear many times in the output.

To address this issue, patterns are reduced to a much smaller group that still collectively spans the search space. This is done by making use of a clustering method based on a 2-approximate solution to the k-center problem. Each of clusters obtained at the end of this process corresponds to an approximate pattern that is retained.

Figure 10:
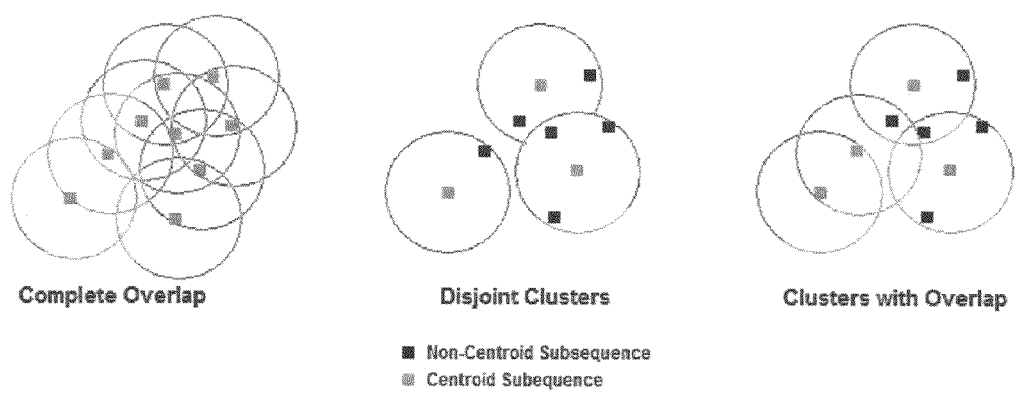
FIG. 10 illustrates how techniques to merge clusters can be used at the end of the first LSH iteration to reduce overlap.

The LSH iterations that follow find approximate matches to the subsequences in Φ. It is important to note that while clustering reduces a large number of overlapping approximate patterns to a much smaller group, the clusters formed during this process may still overlap. This overlap corresponds to missed approximate matches that do not hash to a single bucket during the first LSH iteration. Techniques to merge clusters can be used at the end of the first LSH iteration to reduce overlap. In our work, we tolerate small amounts of overlap between clusters to more thoroughly span the search space. FIG. 10 illustrates the clustering process.

The first method was evaluated to find conserved activity on a population of patients who experienced sudden cardiac death, and attempted to discover electrocardiographic activity that may be associated with the endpoint of death. To assess the predictive patterns discovered, the likelihood scores for patterns in the sudden death population was compared against control populations of normal individuals and those with non-fatal supraventricular arrhythmias. Our results indicate that this method may be able to identify clinically relevant information even in the absence of significant prior knowledge.

The second method was evaluated to find conserved activity on datasets from different applications to discover sequential patterns for classification. For cardiovascular data from patients admitted with acute coronary syndromes, the method identified approximately conserved sequences of morphologic distances that were predictive of future death in a test population. These results indicate that the methods may allow for an unsupervised approach to learning interesting dissimilarities between positive and negative examples that may have a functional role.

The above methods provide ways of finding patterns with predictive power. Other methods are used to identify individual patients with clusters of patients with similar physiological signals. The basis of these methods is a novel metric that quantifies the extent to which the long-term recordings from two patients differ. The pairwise differences are used to partition patients into groups whose recordings exhibit similar characteristics and potentially common risk profiles.

One embodiment predicts that those patients whose long-term electrocardiograms did not match the dominant group in the population, are at increased risk of adverse cardiovascular events. These cases have a high electrocardiographic mismatch relative to the majority of the patients in the population, and form one or more subgroups that are suspected to be at an increased risk of adverse events in the future.

This approach is orthogonal to conventional methods that use specialized high risk features. Firstly, it does not require the presence of significant prior knowledge. The only assumption is that physiological signals from patients who are at high risk differ from those of the rest of the population. There are no specific assumptions about the nature of these differences. Secondly, the ability to partition patients into groups with similar ECG characteristics and potentially common risk profiles allows a fine-grained understanding of a how a patient's future health may evolve over time. In one embodiment, matching patients to past cases with similar ECG signals could lead to assignments of risk scores for particular events such as death and MI.

In one study, this method was applied to a population of 686 patients suffering non-ST-elevation ACS to search for potentially high risk outliers. When evaluated over a 90 day follow-up, patients in clusters outside the dominant group showed an increased risk of death (HR 4.7, $p<0.01$). This relationship could be observed even after adjusting for baseline clinical characteristics (adjusted HR 3.6, $p=0.038$). Moreover, certain clusters in the high risk group showed an even higher rate of death both relative to the dominant population (HR 23.20, $p<0.01$) and to patients in other non-dominant clusters (HR 9.05, $p<0.01$).

Finally it is possible that the patterns of symbols themselves contain additional information in the form of transitions between the symbols. For example, given two symbolic sequences A and B (where A is from Patient 1 and B is from Patient 2), the mismatch between these sequences can be quantified using the methods described above. These methods take into account both differences in symbols and differences in the frequencies with which these symbols occur. However, they do not capture changes in the transitions between symbols. As an example, consider the case where A is as follows:

. . . ABCABCABCABC . . . .

And B is:

. . . ACBACBACBACB . . . .

In both these cases, the kinds of symbols and the frequency with which these symbols occur is the same across the patients. However, the transitions are different, i.e., in patient 1, an A is always followed by a B and then a C, while in patient 2, it is different. These changes have clinical significance.

Hidden Markov models (HMM) are another method to compare two long-term symbolic sequences to determine transition patterns. Methods known to the art are used to train an HMM for each symbolic sequence, and then compare the HMMs to quantify the difference between the long-term symbolic sequences. The process of clustering patients proceeds as earlier.

In short, instead of the process described above to measure differences between symbolic sequences, HMMs are trained on each symbolic sequence. In both cases, the differences between symbolic sequences allow patients to be grouped together, and to be matched to historical data to provide clinical correlation.

It should be understood that the above-described embodiments and the examples are given by way of illustration, not limitation. For example the use of the ECG study for the explanation of the invention and the results is not intended to be limiting. Various changes and modifications within the scope of the present invention will become apparent to those skilled in the art from the present description.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

TABLE 1

Univariate asssociation between clinical characteristics and MI and death

| | MI | | | Death | | |
|---|---|---|---|---|---|---|
| Parameter | Hazard Ratio | 95% CI | P Value | Hazard Ratio | 95% CI | P Value |
| Age | 1.02 | 0.99-1.05 | 0.120 | 1.09 | 1.04-1.15 | 0.001 |
| Male | 1.79 | 0.80-3.94 | 0.157 | 0.37 | 0.13-1.04 | 0.058 |
| Smoker | 1.27 | 0.63-2.55 | 0.508 | 0.53 | 0.19-1.50 | 0.231 |

TABLE 1-continued

Univariate asssociation between clinical characteristics and MI and death

| Parameter | MI | | | Death | | |
|---|---|---|---|---|---|---|
| | Hazard Ratio | 95% CI | P Value | Hazard Ratio | 95% CI | P Value |
| Hypertension | 1.72 | 0.74-3.95 | 0.205 | 6.67 | 0.88-50.7 | 0.067 |
| Diabetes | 1.03 | 0.47-2.29 | 0.937 | 2.79 | 1.01-7.70 | 0.047 |
| Hyperlipidermia | 0.89 | 0.44-1.79 | 0.750 | 0.66 | 0.24-1.82 | 0.421 |
| CHD | 1.15 | 0.57-2.30 | 0.702 | 0.13 | 0.02-0.96 | 0.046 |
| Prior MI | 1.06 | 0.49-2.29 | 0.876 | 1.95 | 0.69-5.48 | 0.206 |
| Prior Angina | 2.52 | 1.14-5.60 | 0.023 | 2.83 | 0.90-8.88 | 0.076 |
| Index Diagnosis of NSTEMI | 2.07 | 0.93-4.59 | 0.074 | 0.96 | 0.34-2.70 | 0.941 |
| ST Depression >0.5 mm | 0.63 | 0.31-1.27 | 0.195 | 2.75 | 0.88-8.64 | 0.083 |

TABLE 2

Univariate association between ECG parameters and MI and death

| Parameter | MI | | | Death | | |
|---|---|---|---|---|---|---|
| | Hazard Ratio | 95% CI | P Value | Hazard Ratio | 95% CI | P Value |
| Ischemia detected in $1^{st}$ 24 hrs of cECG Recording HRV SDANN | 0.95 | 0.13-6.94 | 0.957 | 4.56 | 1.02-20.41 | 0.047 |
| HRV SDANN (20%) | 1.44 | 0.65-3.21 | 0.371 | 2.88 | 1.03-8.10 | 0.045 |
| HRV SDANN (10%) MV | 2.43 | 1.00-5.94 | 0.050 | 1.63 | 0.36-7.27 | 0.524 |
| LF/HF (20%) | 1.21 | 0.52-2.79 | 0.658 | 4.81 | 1.75-13.28 | 0.002 |
| LF/HF (10%) | 1.88 | 0.72-4.89 | 0.195 | 6.53 | 2.32-18.34 | 0.001 |

TABLE 3

| Parameter | Model 1 | | | | Model 2 | | | |
|---|---|---|---|---|---|---|---|---|
| | Lowest Quintile of MV and HRV | | Lowest Decile of MV and HRV | | Lowest Quintile of MV and HRV | | Lowest Decile of MV and HRV | |
| | HR | P Value | HR | P Value | HR | P Value | HR | P Value |
| Age | 1.05 | 0.094 | 1.06 | 0.093 | 1.06 | 0.032 | 1.07 | 0.040 |
| Male | 0.47 | 0.160 | 0.47 | 0.172 | — | — | — | — |
| Hypertension | 4.09 | 0.181 | 4.81 | 0.138 | — | — | 5.87 | 0.089 |
| Diabetes | 1.39 | 0.554 | 1.65 | 0.364 | — | — | — | — |
| CHD | 0.11 | 0.053 | 0.16 | 0.088 | 0.13 | 0.063 | 0.17 | 0.089 |
| Prior Angina | 3.14 | 0.068 | 3.00 | 0.083 | 3.50 | 0.034 | 3.25 | 0.047 |
| ST Dep > 0.5 mm | 1.29 | 0.675 | 1.11 | 0.863 | — | — | — | — |
| Ischemia detected on cECG | 4.29 | 0.069 | 3.56 | 0.109 | 4.47 | 0.056 | — | — |
| HRV SDANN | 2.46 | 0.099 | 1.08 | 0.924 | 2.58 | 0.078 | — | — |
| MV LF/HF | 4.10 | 0.009 | 5.37 | 0.002 | 3.75 | 0.014 | 5.14 | 0.002 |

Association between clinical and ECG variables and death using two multivariable models. Model 1 included all variables associated with death (p <0.1). Model 2 utilized stepwise backward regression.

TABLE 4

| Patient | N | Atr | Ven | Bbb | Jct | Oth | Mis | Mis % |
|---|---|---|---|---|---|---|---|---|
| 100 | 2234/2234 | 30/33 | | | | | 3/2267 | 0.13% |
| 101 | 1852/1852 | 3/3 | | | | | 0/1855 | 0.00% |
| 102 | 14/99 | | 4/4 | | | 2077/2079 | 87/2182 | 3.99% |
| 103 | 2076/2076 | | | | | | 0/2076 | 0.00% |
| 104 | 51/163 | | | | | 2027/2040 | 125/2203 | 5.67% |
| 105 | 2530/2534 | | 39/40 | | | | 5/2574 | 0.19% |
| 106 | 1500/1500 | | 508/511 | | | | 3/2011 | 0.15% |

TABLE 4-continued

| Patient | N | Atr | Ven | Bbb | Jct | Oth | Mis | Mis % |
|---|---|---|---|---|---|---|---|---|
| 107 | | | 59/59 | | | 2074/2075 | 1/2134 | 0.05% |
| 108 | 1748/1748 | 1/4 | 17/18 | | | | 4/1770 | 0.23% |
| 109 | | | 37/40 | 2486/2486 | | | 3/2526 | 0.12% |
| 111 | 2117/2117 | | | | | | 0/2117 | 0.00% |
| 112 | 2533/2533 | | | | | | 0/2533 | 0.00% |
| 113 | 1782/1782 | 5/5 | | | | | 0/1787 | 0.00% |
| 114 | 1815/1815 | 4/8 | 47/48 | | | | 5/1871 | 0.27% |
| 115 | 1946/1946 | | | | | | 0/1946 | 0.00% |
| 116 | 2281/2281 | | 107/107 | | | | 0/2388 | 0.00% |
| 117 | 1528/1528 | | | | | | 0/1528 | 0.00% |
| 118 | | 82/96 | 16/16 | 2147/2161 | | | 28/2273 | 1.23% |
| 119 | 1540/1540 | | 443/443 | | | | 0/1983 | 0.00% |
| 121 | 1858/1858 | | | | | | 0/1858 | 0.00% |
| 122 | 2475/2475 | | | | | | 0/2475 | 0.00% |
| 123 | 1510/1510 | | | | | | 0/1510 | 0.00% |
| 124 | | | 52/52 | 1523/1526 | 6/34 | | 31/1612 | 1.92% |
| 200 | 1737/1739 | 1/29 | 796/815 | | | | 49/2583 | 1.90% |
| 201 | 1605/1605 | 65/76 | 184/185 | | 3/11 | | 20/1877 | 1.07% |
| 202 | 2043/2046 | 32/48 | 18/20 | | | | 21/2114 | 0.99% |
| 203 | 2432/2442 | | 318/345 | | | | 37/2787 | 1.33% |
| 205 | 2564/2565 | 1/3 | 76/77 | | | | 4/2645 | 0.15% |
| 207 | | 114/116 | 190/208 | 1538/1559 | | | 41/1883 | 2.18% |
| 208 | 1507/1575 | | 1327/1348 | | | | 89/2923 | 3.04% |
| 209 | 2603/2617 | 317/383 | | | | | 80/3000 | 2.67% |
| 210 | 2411/2416 | 14/21 | 164/183 | | | | 31/2620 | 1.18% |
| 212 | 920/920 | | | 1821/1824 | | | 3/2744 | 0.11% |
| 213 | 2632/2635 | 4/28 | 321/581 | | | | 287/3244 | 8.85% |
| 214 | | | 260/261 | 1980/1993 | | | 14/2254 | 0.62% |
| 215 | 3190/3191 | | 156/159 | | | | 4/3350 | 0.12% |
| 217 | 229/242 | | 138/157 | | | 1720/1802 | 114/2201 | 5.18% |
| 219 | 2077/2077 | 0/7 | 31/63 | | | | 39/2147 | 1.82% |
| 220 | 1942/1947 | 91/93 | | | | | 7/2040 | 0.34% |
| 221 | 2028/2028 | | 381/382 | | | | 1/2410 | 0.04% |
| 222 | 1939/1977 | 121/187 | | | 125/216 | | 195/2380 | 8.19% |
| 223 | 2021/2025 | 20/89 | 462/484 | | | | 95/2598 | 3.66% |
| 228 | 1685/1687 | 0/3 | 366/371 | | | | 10/2061 | 0.49% |
| 230 | 2249/2249 | | | | | | 0/2249 | 0.00% |
| 231 | 312/312 | | | 1246/1247 | | | 1/1559 | 0.06% |
| 232 | | 1407/1423 | | 435/437 | | | 18/1860 | 0.97% |
| 233 | 2219/2220 | 0/7 | 814/828 | | | | 22/3055 | 0.72% |
| 234 | 2695/2696 | | 3/3 | | 35/50 | | 16/2749 | 0.58% |
| Total Beats | 76430/76802 | 2312/2662 | 7334/7808 | 13176/13233 | 169/311 | 7898/7996 | 1493/108812 | 1.37% |
| Total Patients | 41/41 | 18/21 | 29/29 | 8/8 | 4/4 | 4/4 | | |

TABLE 5

| | N | L | R | A | a | V | P | f | F | j |
|---|---|---|---|---|---|---|---|---|---|---|
| Percentage of total patients detected | 100.0 | 100.0 | 100.0 | 84.21 | 100.0 | 100.0 | 100.0 | 100.0 | 75.0 | 100.0 |
| Percentage of total beats detected | 99.52 | 99.50 | 99.67 | 87.30 | 85.11 | 96.80 | 99.91 | 78.75 | 46.69 | 56.96 |

TABLE 6

| | N | V | P | J | F |
|---|---|---|---|---|---|
| Percentage of total clust. detected | 100.0 | 100.0 | 100.0 | 100.0 | 100.0 |
| Percentage of total beats detected | 99.91 | 96.51 | 98.84 | 100.0 | 100.0 |

What is claimed is:

1. A method of predicting patient outcome from a physiological segmentable signal of a patient comprising the steps of:

obtaining the physiological segmentable signal from a medical device in communication with the patient;

segmenting, using a processor, the physiological segmentable signal into a plurality of separate components;

calculating, using a processor, a time series of a morphological distance between adjacent separate components of the plurality of separate components, the morphologic distance between adjacent separate components being determined by an energy difference in the adjacent separate components, and the energy difference between adjacent separate components being determined by physiological dynamic time warping; and predicting, using a processor, patient outcome at least in response to the time series of the morphological distance.

2. The method of claim 1 wherein the physiological segmentable signal is an ECG and where each segmentable component is a heartbeat.

3. The method of claim 2 wherein segments of the ECG that are unlikely to represent cardiac activity are rejected.

4. The method of claim 2 wherein the step of predicting patient outcome is performed with an overall risk measure calculated in response to an ECG risk measure and a plurality of other metrics.

5. The method of claim 1 wherein a higher variability of morphologic distance indicates a higher probability of a worse patient outcome.

6. The method of claim 1 wherein the predicted patient outcome is selected from a group consisting of death, arrhythmia, myocardial ischemia and myocardial infarction.

7. The method of claim 1 wherein the method further comprises the step of predicting patient outcome in response to combining, using a processor, morphologic distance variability with a clinical predictor.

8. The method claim 7 wherein the other clinical predictor is a TIMI risk assessment.

9. The method of claim 1 wherein the step of predicting patient outcome is performed with a risk measure calculated in response to morphological distance variability and other measures.

10. The method of claim 1 further comprising the steps of noise and artifact removal.

11. The method of claim 1 wherein the physiological signal is a respiration signal.

12. The method of claim 11 wherein each component is a breath.

13. The method of claim 1 wherein an information class is derived from at least one of: standard features of clinical significance and non-standard features of clinical significance.

14. The method of claim 1 wherein the components are grouped into information classes using clustering.

15. The method of claim 1 wherein the plurality of components is grouped into a predetermined number of information classes.

16. The method of claim 1 wherein the plurality of components is grouped into a number of information classes which is not predetermined.

17. The method of claim 1 further comprising the step of associating a representative component to an information class.

18. The method of claim 17 wherein the information class is formed using a clustering technique and the representative component of the information class is a centroid of the cluster.

19. The method of claim 1 further including the steps of repeating the steps for a plurality of patients having a common components of interest;

assigning a symbol to each of the components of interest to for a symbolic series and examining the symbolic series for commonalities of the common components of interest.

20. The method of claim 19 wherein a commonality is a pattern that is approximately conserved preceding the event of interest.

21. The method of claim 19 wherein commonality is determined using active regions and a two-layer Gibbs sampling algorithm.

22. The method of claim 19 wherein both positive and negative examples are used to determine commonalities.

23. The method of claim 1 wherein an information class is derived from information in a time and/or frequency domain of the physiological segmentable signal.

24. The method of claim 23 wherein the information class is assigned a symbol and wherein a sequence of symbols has significance due to at least one of: the number of distinct symbols represented and the distribution of symbols represented.

25. The method of claim 23 wherein the information class is assigned a symbol and wherein a sequence of symbols has significance due to its entropy.

26. The method of claim 23 wherein the information class is assigned a symbol and wherein a sequence of symbols has significance due to the pattern of symbols represented.

27. The method of claim 24 in which an examination of the symbolic series is performed on signals from a group consisting of signals from different time periods for the same patient and signals from different patients.

28. The method of claim 24 in which an examination of the symbolic series is performed using methods selected from the group of locality sensitive hashing, clustering using a 2-approximate solution of the k-center problem and sequential statistics.

29. The method of claim 24 wherein the examination of the symbolic sequences is based upon comparing patients to other patients with related symbolic sequences.

30. The method of claim 24 further comprising associating a representative component to each information class and wherein the matching is performed based upon characteristics of a group consisting of the differences among the representative components of the information classes, the distribution of symbols, and hidden Markov models.

31. The method of claim 27 wherein patients are partitioned into a dominant group and a plurality of non-dominant groups.

32. The method of claim 27 wherein a new patient is assigned a risk profile derived from matching the new patient's physiological signal to groups derived from historical data.

33. The method of claim 31 wherein patients in non-dominant groups are assessed as being at elevated risk.

34. A method of predicting patient outcome from a physiological segmentable signal of a patient comprising the steps of:

obtaining the physiological segmentable signal from a medical device in communication with the patient;

segmenting, using a processor, the physiological segmentable signal into a plurality of separate components;

calculating, using a processor, a time series of a morphological distance between adjacent separate components of the plurality of separate components, the morphologic distance between adjacent separate components being determined by an energy difference in the adjacent separate components, and the energy difference between adjacent separate components being determined by physiological dynamic time warping; and summarizing, using a processor, the information in the time series.

35. The method of claim 34 further comprising the step of predicting patient outcome in response to the summarized time series information.

36. The method of claim 34 further comprising treating the patient by a clinician and measuring efficacy of treatment in response to the summarized time series information by the processor.

37. The method of claim 34 wherein the step of summarizing of time series information comprises the steps of determining the low frequency power and high frequency power in the time series and calculating a ratio of low frequency power to high frequency power for the time series.

38. The method of claim 34 wherein the summarizing of the time series information comprises the steps of determining the low frequency power and high frequency power in the time series and calculating energy in a diagnostic frequency range.

39. The system of claim 34 wherein an information class is derived from information in one of a time and frequency domain of the physiological segmentable signal.

40. The system of claim 39 wherein each information class is assigned a symbol and wherein the sequence of symbols has significance due to at least one of: the number of distinct symbols represented and the distribution of symbols represented.

41. The system of claim 40 wherein the symbolic sequence has significance due to a group consisting of its entropy and the pattern of symbols represented.

42. The system of claim 34 wherein an information class is one of standard clinical significance and non-standard clinical significance.

43. The system of claim 34 wherein the components are grouped into information classes using clustering.

44. The system of claim 34 wherein the plurality of components is grouped into a predetermined number of information classes.

45. The system of claim 34 wherein the plurality of components is grouped into a number of information classes which is not predetermined.

46. The system of claim 34 further comprising associating a representative component to each information class.

47. A system for predicting patient outcome from a physiological segmentable signal of a patient comprising:
a processor, the processor performing the operations of:
obtaining the physiological segmentable signal of the patient;
segmenting the physiological segmentable signal into a plurality of separate components; and
calculating a time series of a morphological distance between adjacent separate components of the plurality of separate components,
the morphologic distance between adjacent separate components being determined by an energy difference in the adjacent separate components,
the energy difference between adjacent separate components being determined by physiological dynamic time warping; and
predicting patient outcome in response to the time series.

48. The system of claim 47 wherein the processor further predicts patient outcome in response to the time series of the morphological distance.

49. The system of claim 47 wherein the processor, after the patient has been treated by a clinician, further performs the step of determining the efficacy of treatment in response to the time series of morphological distance.

50. The system of claim 47 wherein the physiological segmentable signal is an ECG and where each component is a heartbeat.

51. The system of claim 47 wherein the higher the variability of morphologic distance indicates a higher probability of a worse the patient outcome.

52. A system for predicting patient outcome from a physiological segmentable signal of a patient comprising
a processor, the processor performing the operations of:
obtaining the physiological segmentable signal of the patient;
segmenting the physiological segmentable signal into a plurality of separate components;
calculating a time series of a morphological distance between adjacent separate components of the plurality of separate components,
the morphologic distance between adjacent separate components being determined by the energy difference in the adjacent separate components, and
the energy difference between adjacent separate components being determined by physiological dynamic time warping; and
summarizing the information in the time series.

53. The system of claim 52 wherein the processor further performs the step of predicting patient outcome in response to the summarized time series information.

54. The system of claim 52 wherein the processor, after the patient has been treated by a clinician, further performs the step of determining efficacy of treatment in response to the summarized time series information.

55. The system of claim 52 wherein the physiological signal is an ECG signal.

56. The system of claim 55 wherein the each component is a heartbeat.

57. The system of claim 52 wherein the physiological signal is a respiration signal.

58. The system of claim 57 wherein the each component is a breath.

* * * * *